(12) United States Patent
Sun et al.

(10) Patent No.: US 11,819,357 B2
(45) Date of Patent: *Nov. 21, 2023

(54) SYSTEM AND METHOD FOR PET CORRECTION

(71) Applicant: SHANGHAI UNITED IMAGING HEALTHCARE CO., LTD., Shanghai (CN)

(72) Inventors: Yixing Sun, Shanghai (CN); Shitao Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/305,666

(22) Filed: Jul. 12, 2021

(65) Prior Publication Data

US 2021/0338188 A1 Nov. 4, 2021

Related U.S. Application Data

(63) Continuation of application No. 16/236,503, filed on Dec. 30, 2018, now Pat. No. 11,058,391, which is a
(Continued)

(51) Int. Cl.
*A61B 6/00* (2006.01)
*G06T 7/80* (2017.01)
*G01T 1/29* (2006.01)
*A61B 6/03* (2006.01)
*G01T 1/164* (2006.01)
*G01T 7/00* (2006.01)

(52) U.S. Cl.
CPC ........... *A61B 6/585* (2013.01); *A61B 6/037* (2013.01); *G01T 1/1648* (2013.01); *G01T 1/2985* (2013.01); *G01T 7/005* (2013.01); *G06T 7/80* (2017.01); *G06T 2207/10104* (2013.01)

(58) Field of Classification Search
CPC ....... A61B 6/037; A61B 6/585; G01T 1/1648; G01T 1/2985; G06T 2207/10104; G06T 7/005; G06T 7/80
See application file for complete search history.

(56) References Cited

U.S. PATENT DOCUMENTS 5,834,779 A 11/1998 Shao et al.
6,740,883 B1 5/2004 Stodilka et al.
(Continued)

FOREIGN PATENT DOCUMENTS

CN 106256327 A 12/2016
JP 2006189274 A 7/2006

OTHER PUBLICATIONS

International Search Report in PCT/CN2017/108618 dated Jun. 28, 2018, 4 pages.
(Continued)

*Primary Examiner* — Blake C Riddick
(74) *Attorney, Agent, or Firm* — METIS IP LLC

(57) ABSTRACT

A method for determining a correction profile of an imaging device may include obtaining first data relating to the imaging device; comparing the first data and a first condition; obtaining, based on the comparison, a first correction profile relating to the imaging device; and calibrating, based on the first correction profile, the imaging device.

18 Claims, 16 Drawing Sheets

Related U.S. Application Data continuation of application No. PCT/CN2017/108618, filed on Oct. 31, 2017.

(56) References Cited

U.S. PATENT DOCUMENTS

| | | |
|---|---|---|
| 2006/0138315 A1 | 6/2006 | Williams et al. |
| 2007/0147589 A1 | 6/2007 | Thielemans |
| 2008/0075347 A1 | 3/2008 | Ruhrnschopf |
| 2009/0003655 A1 | 1/2009 | Wollenweber |
| 2009/0110256 A1 | 4/2009 | Thielemans et al. |
| 2010/0193696 A1 | 8/2010 | Blevis et al. |
| 2010/0220909 A1 | 9/2010 | Thielemans et al. |
| 2011/0135179 A1 | 6/2011 | Ross et al. |
| 2011/0142304 A1 | 6/2011 | Stearns |
| 2011/0142367 A1 | 6/2011 | Stearns et al. |
| 2012/0153165 A1 | 6/2012 | Ott |
| 2013/0087697 A1 | 4/2013 | Xie et al. |
| 2013/0261440 A1 | 10/2013 | Georgi et al. |
| 2014/0014828 A1 | 1/2014 | Bredno et al. |
| 2014/0099009 A1 | 4/2014 | Lonn et al. |
| 2014/0153806 A1 | 6/2014 | Glielmi et al. |
| 2014/0334702 A1 | 11/2014 | El Fakhri et al. |
| 2015/0036789 A1* | 2/2015 | Panin .................. G06T 11/006 378/4 |
| 2015/0073272 A1* | 3/2015 | Corbeil .................. A61B 6/42 250/361 R |
| 2015/0301201 A1 | 10/2015 | Rothfuss et al. |
| 2016/0038113 A1 | 2/2016 | Fan et al. |
| 2017/0018099 A1 | 1/2017 | Heukensfeldt Jansen et al. |
| 2017/0082759 A1 | 3/2017 | Lyu et al. |
| 2019/0049605 A1 | 2/2019 | Dong |
| 2019/0059843 A1 | 2/2019 | Watanabe et al. |
| 2019/0150877 A1 | 5/2019 | Sun et al. |

OTHER PUBLICATIONS

Written Opinion in PCT/CN2017/108618 dated Jun. 28, 2018, 4 pages.

* cited by examiner

SYSTEM AND METHOD FOR PET CORRECTION

CROSS-REFERENCE TO RELATED APPLICATIONS

This application is a continuation of U.S. application Ser. No. 16/236,503, filed on Dec. 30, 2018, which is a continuation of International Application No. PCT/CN2017/108618, filed on Oct. 31, 2017. The entire contents of the application are incorporated herein by reference.

TECHNICAL FIELD

The present disclosure generally relates to nuclear medical imaging, and more particularly, a system and method for correction relating to positron emission tomography (PET) imaging.

BACKGROUND

Nuclear medicine imaging is widely used in diagnosis and treatment of various medical conditions based on images acquired by using radiation emission. PET is an exemplary nuclear medicine imaging technique. PET is used to generate images that may reflect metabolic activities of a specific organ or tissue (e.g., a tumor). A detector used in PET may receive radiation rays (e.g., γ rays) generated from a patient's body indirectly by tracer molecules and provide information relating to the metabolic activities at locations of the tracer molecules, which in turn provides functional information of the patient. A PET detector may generate electrical signals based on the radiation rays, and then the electrical signals may be converted into data to be used to reconstruct a PET image.

The quality of a PET image may relate to a performance parameter (e.g., a sensitivity, a time resolution, an energy resolution, a spatial resolution, etc.) of the PET detector that has acquired the data leading to the PET image. For example, the quality of a PET image assessed in terms of, e.g., noises, artifacts, etc., may depend on the sensitivity of the PET detector. In some embodiments, a correction relating to the PET detector may be performed. It may be desirable to provide systems and methods for determining a correction relating to a PET detector.

SUMMARY

According to an aspect of the present disclosure, a method for determining a correction profile of an imaging device including a detector, the detector including detector blocks, each detector block including at least one detecting element is provided. The method may be implemented on at least one machine each of which has at least one processor and storage. The method may include obtaining first data relating to the imaging device; comparing the first data and a first condition; obtaining, based on the comparison, a first correction profile relating to the imaging device; and calibrating, based on the first correction profile, the imaging device.

In some embodiments, the obtaining, based on the comparison, a first correction profile relating to the imaging device, may further include determining, based on the first data relating to the imaging device, that the imaging device satisfies the first condition; and obtaining, in response to the determination that the imaging device satisfies the first condition, the first correction profile.

In some embodiments, the first data may include a response rate of each of the detector blocks, and the determining, based on first data relating to the imaging device, that the imaging device satisfies the first condition may include acquiring a first group of detector blocks; each detector block of the first group having a response rate lower than a second threshold or exceeding a third threshold; and determining whether a detector block count of the detector blocks belonging to the first group exceeds a first threshold.

In some embodiments, the first data relating to the imaging device may include second scanning data relating to a second subject detected by the imaging device.

In some embodiments, the determining, based on first data relating to the imaging device, that the imaging device satisfies a first condition, may include extracting first feature data from the second scanning data relating to the second subject; and determining, based on the first feature data, whether the imaging device satisfies the first condition.

In some embodiments, the first feature data may relate to at least one of an energy peak corresponding to each of the at least one detecting element, a position of each of the detector blocks, or a time offset relating to a pair of detecting elements corresponding to a line of response.

In some embodiments, the determining, based on the first feature data, that the imaging device satisfies the first condition may include determining a difference between the first feature data and reference feature data; and determining whether the difference between the first feature data and reference feature data exceeds a fourth threshold.

In some embodiments, the first condition may relate to a parameter of the imaging device, and the parameter may include at least one of a sensitivity of the detector, a spatial resolution of the imaging device, an energy resolution of the imaging device, or a time resolution of the imaging device.

In some embodiments, the obtaining, based on the comparison, a first correction profile relating to the imaging device, may further include acquiring third scanning data relating to a third subject detected by the imaging device e, the third scanning data satisfying a second condition; and determining, based on the third scanning data relating to the third subject, the first correction profile relating to the imaging device.

In some embodiments, the third scanning data may include a radiation event count, the second condition relates to the radiation event count, and the third scanning data satisfying a second condition may include the radiation event count equaling or exceeding a fifth threshold.

In some embodiments, the calibrating, based on the first correction profile, the imaging device may include updating a second correction profile stored in the imaging device by the first correction profile relating to the imaging device.

According to an aspect of the present disclosure, a method for determining a correction profile of an imagine device including a detector, the detector including detector blocks, each detector block including at least one detecting element is provided. The method may be implemented on at least one machine each of which has at least one processor and storage. The method may include acquiring first scanning data from a subject detected by the detector; comparing the first scanning data and the first condition; determining, based on the comparison, a correction profile relating to the imaging device; and calibrating; based on the correction profile, the imaging device.

In some embodiments, the determining, based on the comparison; a correction profile relating to the imaging device, may further include determining that the first scanning data from the subject satisfies the first condition; and determining, based on the first scanning data, the correction profile.

In some embodiments, the first scanning data may include a radiation event count, and the determining that the first scanning data from the subject satisfies a first condition may include determining whether the radiation event count of the first scanning data equals or exceeds a first threshold.

In some embodiments, the first scanning data may include a body mass index of the subject, and the determining that the first scanning data from the subject satisfies the first condition may include determining whether the body mass index of the subject is in a range from a second threshold to a third threshold.

In some embodiments, the first scanning data may relate to a distribution of the radiation events corresponding to lines of response, and the determining that the first scanning data from the subject satisfies the first condition may include determining whether a half width of the distribution of the radiation events corresponding to the lines of response equals or exceeds a fourth threshold.

In some embodiments, the obtaining, based on the first scanning data relating to the subject, a correction profile relating to the imaging device may further include extracting feature data from the first scanning data; determining, from the first scanning data and based on the feature data, second scanning data relating to the radiation events; and determining, based on the second scanning data, the correction profile relating to the imaging device, wherein the correction profile includes a plurality of correction coefficients corresponding to the feature data.

According to an aspect of the present disclosure, a method for determining a correction profile of an imaging device including a detector, the detector including detector blocks, each detector block including at least one detecting element is provided. The method may be implemented on at least one machine each of which has at least one processor and storage. The method may include acquiring first scanning data relating to a subject, the first scanning data relating to radiation events originating from the subject detected by the detector; extracting feature data from the first scanning data; determining, from the first scanning data and based on the feature data, second scanning data relating to radiation events corresponding to the feature data; determining, based on the second scanning data, a correction profile relating to the imaging device, wherein the correction profile includes a plurality of correction coefficients corresponding to the feature data; and calibrating, based on the correction profile; the imaging device.

In some embodiments, the feature data may relate to at least one of energy information of one of the radiation events, a position of one of the radiation events corresponding to the detector, or a time offset relating to a pair of detecting elements corresponding to a line of response.

In some embodiments, the second scanning data may include a first sub-set of data and a second sub-set of data, the first sub-set of data being used in determining the correction profile relating to the imaging device, the second sub-set of data being determined by excluding the first sub-set of data from the second scanning data, and the preprocessing second scanning data to obtain the first scanning data may include removing, from the second scanning data, the second sub-set of data.

According to an aspect of the present disclosure, a system for determining a correction profile is provided. The system may include a computer-readable storage medium storing executable instructions and at least one processor in communication with the computer-readable storage medium. When the executable instructions are executed, the executable instructions may cause the system to implement a method. The method may include obtaining first data relating to an imaging device, comparing the first data and a first condition, obtaining, based on the comparison, a first correction profile relating to the imaging device, and calibrating, based on the first correction profile, the imaging device.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include obtaining first data relating to an imaging device, comparing the first data and a first condition, obtaining, based on the comparison, a first correction profile relating to the imaging device, and calibrating, based on the first correction profile, the imaging device.

According to an aspect of the present disclosure, a system for determining a correction profile is provided. The system may include a data acquisition module configured to obtain first data relating to an imaging device; a detector assessment module configured to comparing the first data and a first condition; a correction profile determination module configured to obtain, in response to the determination that the imaging device satisfies the first condition, a first correction profile relating to the imaging device; and a data correction module configured to calibrate, based on the first correction profile, the imaging device.

According to an aspect of the present disclosure, a system for determining a correction profile is provided. The system may include a computer-readable storage medium storing executable instructions and at least one processor in communication with the computer-readable storage medium. When the executable instructions are executed, the executable instructions may cause the system to implement a method. The method may include acquiring first scanning data relating to a subject detected by a detector of an imaging device; comparing the first scanning data and the first condition; determining, based on the comparison, a correction profile relating to the imaging device; and calibrating, based on the correction profile, the imaging device.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include acquiring first scanning data relating to a subject detected by a detector of an imaging device; comparing the first scanning data and the first condition; determining, based on the comparison, a correction profile relating to the imaging device; and calibrating, based on the correction profile, the imaging device.

According to an aspect of the present disclosure, a system for determining a correction profile is provided. The system may include a data acquisition module configured to obtain first scanning data relating to a subject; a data assessment module configured to comparing the first scanning data and a first condition; and a correction profile determination module configured to obtain, based on the comparison, a correction profile relating to an imaging device.

According to an aspect of the present disclosure, a system for determining a correction profile is provided. The system may include a computer-readable storage medium storing executable instructions and at least one processor in communication with the computer-readable storage medium. When the executable instructions are executed, the executable instructions may cause the system to implement a method. The method may include acquiring first scanning data relating to a subject, the first scanning data relating to radiation events originating from the subject detected by a detector of an imaging device; extracting feature data from the first scanning data; determining, from the first scanning data and based on the feature data, second scanning data relating to radiation events corresponding to the feature data; determining, based on the second scanning data, a correction profile relating to the imaging device, wherein the correction profile includes a plurality of correction coefficients corresponding to the feature data; and calibrating, based on the correction profile, the imaging device.

According to another aspect of the present disclosure, a non-transitory computer readable medium is provided. The non-transitory computer readable medium may include executable instructions. When the instructions are executed by at least one processor, the instructions may cause the at least one processor to implement a method. The method may include acquiring first scanning data relating to a subject, the first scanning data relating to radiation events originating from the subject detected by a detector of an imaging device; extracting feature data from the first scanning data; determining, from the first scanning data and based on the feature data, second scanning data relating to radiation events corresponding to the feature data; determining, based on the second scanning data, a correction profile relating to the imaging device, wherein the correction profile includes a plurality of correction coefficients corresponding to the feature data; and calibrating, based on the correction profile, the imaging device.

According to an aspect of the present disclosure, a system for determining a correction profile is provided. The system may include a data acquisition module configured to acquire first scanning data relating to a subject, the scanning data being detected by a detector of an imaging device; and a data processing module configured to extracting feature data from the first scanning data; determining, from the first scanning data and based on the feature data, second scanning data relating to radiation events corresponding to the feature data; determining, based on the second scanning data, a correction profile relating to the imaging device, wherein the correction profile includes a plurality of correction coefficients corresponding to the feature data; and calibrating, based on the correction profile, the imaging device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
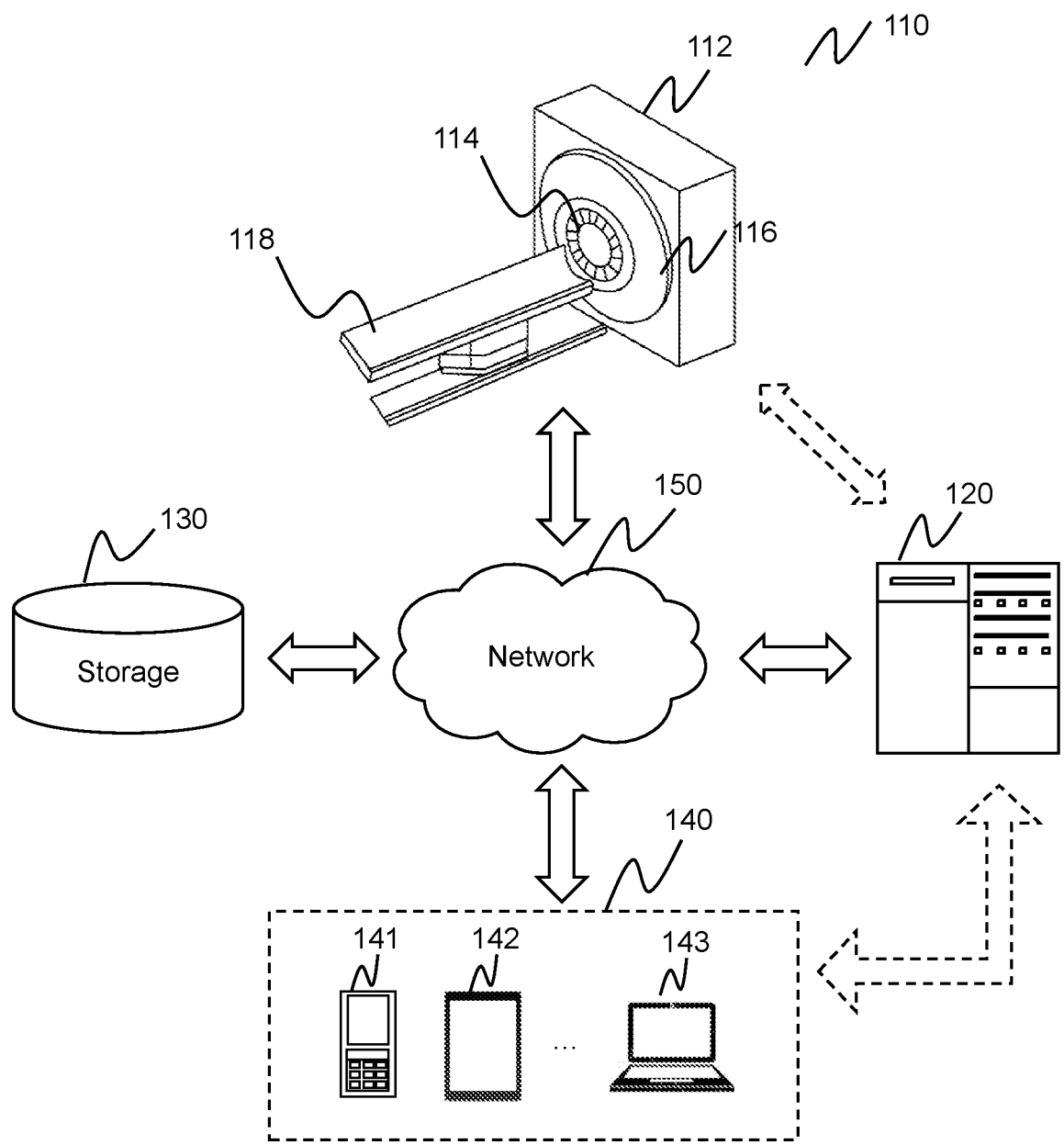
FIG. 1 is a schematic diagram illustrating an exemplary PET system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block; it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and methods for imaging. In some embodiments, the imaging system may include a single-modality imaging system, such as a positron emission tomography (PET) system, a single photon emission computed tomography-computed tomography (SPECT), or the like, or any combination thereof. In some embodiments, the imaging system may include a multi-modality imaging system such as, for example, a positron emission tomography-computed tomography (PET-CT) system, a positron emission tomography-magnetic resonance imaging (PET-MRI) system, a single photon emission computed tomography-computed tomography (SPECT-CT) system, a digital subtraction angiography-positron emission tomography (DSA-PET) system, etc. It should be noted that the PET system 100 described below is merely provided for illustration purposes, and not intended to limit the scope of the present disclosure.

For illustration purposes, the disclosure describes systems and methods for performing a correction relating to an imaging device. In some embodiments, the system may obtain a correction profile for correcting the imaging device (e.g., a PET device). For example, the system may determine whether the imaging device needs to be corrected. If the system determines that the imaging device needs to be corrected, the system may obtain a correction profile generated based on second scanning data relating to a second subject that is different from the first subject being imaged. The second scanning data may be assessed according to one or more conditions before it is used to generate the correction profile. Then, the system may obtain the first scanning data based on the correction profile. In some embodiments, the system may obtain scanning data relating to a subject based on a correction profile relating to an imaging device. For example, the system may determine whether the imaging device needs to be corrected. If the imaging device needs to be corrected, the system may generate a first correction profile based on first scanning data relating to a first subject. The system may adjust the imaging device by updating a second correction profile stored in the imaging device with the first correction profile. Then, the system may obtain second scanning data relating to a second subject based on the first correction profile. The second subject may be different from the first subject.

For illustration purposes, the following description is provided to help better understanding a PET imaging system. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

FIG. 1 is a schematic diagram illustrating an exemplary PET system 100 according to some embodiments of the present disclosure. As shown, the PET system 100 may include a scanner 110, a processing device 120, storage 130, one or more terminals 140, and a network 150. In some embodiments, the scanner 110, the processing device 120, the storage 130, and/or the terminal 140 may be connected to and/or communicate with each other via a wireless connection (e.g., the network 150), a wired connection, or a combination thereof. The connection between the components in the PET system 100 may be variable. Merely by way of example, the scanner 110 may be connected to the processing device 120 through the network 150, as illustrated in FIG. 1. As another example, the scanner 110 may be connected to the processing device 120 directly. As a further example, the storage 130 may be connected to the processing device 120 through the network 150, as illustrated in FIG. 1, or connected to the processing device 120 directly. As still a further example, a terminal 140 may be connected to the processing device 120 through the network 150, as illustrated in FIG. 1, or connected to the processing device 120 directly.

The scanner 110 may scan at least part of a subject, and/or generate data relating to the subject. In some embodiments, the scanner 110 may be an imaging device, for example, a PET device, a PET-CT device, a PET-MRI device, etc. The scanner 110 may include a gantry 112, a detector 114, an electronics module 116, a table 118, and/or other components not shown, for example a cooling assembly. In the present disclosure, "object" and "subject" are used interchangeably. The subject may be biological or non-biological. For example, the subject may include a patient, a man-made object, etc. As another example, the subject may include a specific portion, organ, and/or tissue of the patient. For example, the subject may include the head, the brain, the neck, the body, a shoulder, an arm, the thorax, the heart, the stomach, a blood vessel, a soft tissue, a knee, a foot, or the like, or a combination thereof, of the patient.

The gantry 112 may support one or more parts of the scanner 110, for example, the detector 114, the electronics module 116, and/or other components, such as the cooling assembly, etc. The table 118 may support and/or position a subject in a detection region of the scanner 110. The detection region may be formed according to the arrangement of the detector 14 on the gantry 112.

The detector 114 may detect radiation photons (e.g., γ photons) emitted from a subject being examined. In some embodiments, the detector 114 may receive radiation rays (e.g., gamma rays) and generate electrical signals. The detector 114 may include one or more detector modules. A detector module may be arranged in any suitable configuration, for example, a ring, an arc, a rectangle, an array, or the like, or any combination thereof. A detector module may include one or more detector blocks. One or more detector units may be packaged to form a detector block. A detector unit (also referred to as detector element) may include a crystal element and/or a photomultiplier (e.g., a silicon photomultiplier (SiPM), a photomultiplier tube (PMT), etc.). In response to the detection of a photon (e.g., a γ photon) impinging on a detector unit, the detector unit may generate an electric signal. For example, a plurality of crystal elements (also referred to as scintillators) in the detector unit may be configured as a scintillator crystal array (also referred to as a scintillator array). A scintillator may scintillate when a radiation photon (e.g., a γ photon) impinges on the scintillator. The scintillator may absorb the energy of the radiation photon (e.g., a γ photon), and convert the absorbed energy into a certain number of photons. The photomultiplier in the detector unit may convert the certain number of light photons into a scintillation pulse.

The electronics module 116 may collect and/or process electrical signals (e.g., scintillation pulses) generated by the detector 114. The electronics module 116 may include one or more of an adder, a multiplier, a subtracter, an amplifier, a drive circuit, a differential circuit, a integral circuit, a counter, a filter, an analog-to-digital converter (ADC), a lower limit detection (LLD) circuit, a constant fraction discriminator (CFD) circuit, a time-to-digital converter (TDC), a coincidence circuit, or the like, or any combination thereof. The electronics module 116 may convert an analog signal (e.g., an electrical signal generated by the detector 114) relating to a radication photon received by the detector 114 to a digital signal relating to a radiation event. As used herein, a radiation event (also referred to as a single event) may refer to an interation between a radiation photon emitted from a subject and impinging on the detector 114. A pair of radiation photons interacting with two detector blocks along a line of response (LOR) within a coincidence time window may be determined as a coincidence event. The coincidence event may include a true coincidence event, a scatter coincidence event, a random coincidence event, or a combination thereof. The electronics module 116 may compare a plurality of digital signals, analyze the plurality of digital signals, and determine information including, e.g., energy information, interaction position information, and/or information of an interaction time of the impinging photons detected by the detector 114. The electronics module 116 may determine one or more coincidence events based on the energy information, the interaction position information, and/or the interaction time information of the detected impinging photons. The electronics module 116 may determine projection data based on the coincidence events and/or the energy information of the impinging photons detected by the detector 114.

The processing device 120 may process data and/or information obtained from the scanner 110, the storage 130, and/or the terminal 140, For example, the processing device 120 may determine a correction profile based on first scanning data relating to a first subject acquired by an imaging device (e.g., the scanner 110). As another example, the processing device 120 may correct second scanning data relating to a second subject based on a correction profile. As a further example, the processing device 120 may process projection data determined based on corrected scanning data to generate an image. In some embodiments, the processing device 120 may be a single server or a server group. The server group may be centralized or distributed. In some embodiments, the processing device 120 may be local or remote. For example, the processing device 120 may access information and/or data stored in the scanner 110, the terminal 140, and/or the storage 130 via the network 150. As another example, the processing device 120 may be directly connected to the scanner 110, the terminal 140 and/or the storage 130 to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 120 may be implemented by a computing device. In some embodiments, the processing device 120, or a portion of the processing device 120 may be integrated into the scanner 110.

The storage 130 may store data, instructions, and/or any other information. In some embodiments, the storage 130 may store data obtained from the terminal 140 and/or the processing device 120. In some embodiments, the storage 130 may store data and/or instructions that the processing device 120 may execute or use to perform exemplary methods described in the present disclosure. In some embodiments, the storage 130 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the storage 130 may be connected to the network 150 to communicate with one or more other components in the PET system 100 (e.g., the processing device 120, the terminal 140, etc.). One or more components of the PET system 100 may access the data or instructions stored in the storage 130 via the network 150. In some embodiments, the storage 130 may be directly connected to or communicate with one or more other components in the PET system 100 (e.g., the processing device 120, the terminal 140, etc.). In some embodiments, the storage 130 may be part of the processing device 120.

The terminal 140 may include a mobile device 141, a tablet computer 142, a laptop computer 143, or the like, or any combination thereof. In some embodiments, the mobile device 141 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™ a Hololens™, a Gear VR™, etc. In some embodiments, the terminal 140 may be part of the processing device 120.

The network 150 may include any suitable network that can facilitate exchange of information and/or data for the PET system 100. In some embodiments, one or more components of the PET system 100 (e.g., the scanner 110, the terminal 140, the processing device 120, the storage 130, etc.) may communicate information and/or data with one or more other components of the PET system 100 via the network 150. For example, the processing device 120 may obtain image data from the scanner 110 via the network 150. As another example, the processing device 120 may obtain user instructions from the terminal 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Viii-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the PET system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage 130 may be a data storage including cloud computing platforms, such as, public cloud, private cloud, community, and hybrid clouds, etc. However, those variations and modifications do not depart the scope of the present disclosure.

Figure 2:
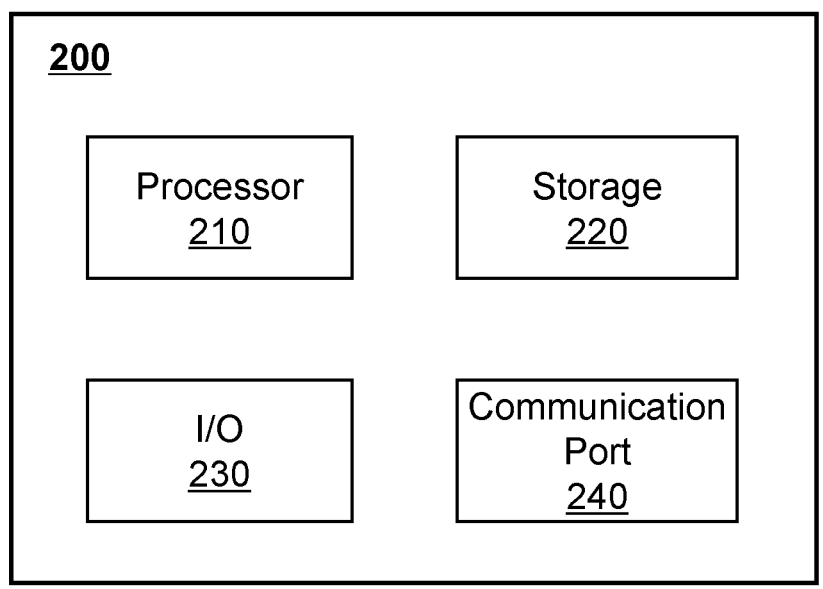
FIG. 2 is a schematic diagram illustrating exemplary hardware and/or software components of an exemplary computing device on which the processing device may be implemented according to some embodiments of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data (e.g., projection data) obtained from the scanner 110, the storage 130, the terminal 140, and/or any other component of the PET system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operation's A and B).

The storage 220 may store data/information obtained from the scanner 110, the storage 130, the terminal 140, and/or any other component of the PET system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing device 120 for determining a correction profile.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 150) to facilitate data communications. The communication port 240 may establish connections between the processing device 120 and the scanner 110, the storage 130, and/or the terminal 140. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
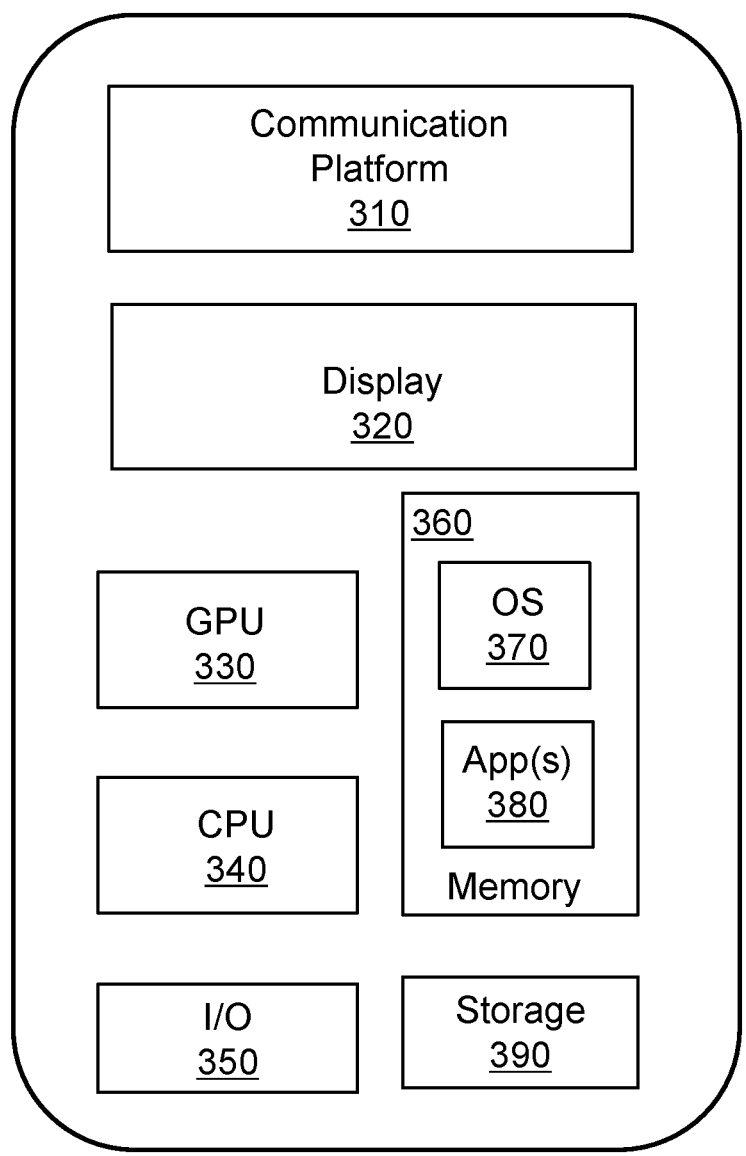
FIG. 3 is a schematic diagram illustrating exemplary hardware and/or software components of an exemplary mobile device on which the terminal(s) may be implemented according to some embodiments of the present disclosure.

FIG. 3 is a schematic diagram illustrating exemplary hardware and/or software components of an exemplary mobile device 300 on which the terminal 140 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 120. User interactions with the information stream may be achieved via the I/O 350 and provided to the processing device 120 and/or other components of the PET system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
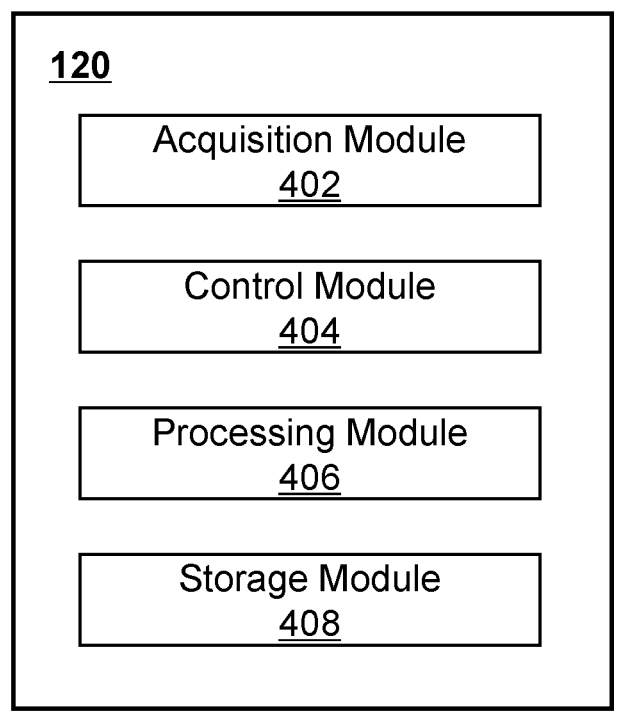
FIG. 4 is a block diagram illustrating an exemplary processing device according to some embodiments of the present disclosure.

FIG. 4 is a block diagram illustrating an exemplary processing device 120 according to some embodiments of the present disclosure. The processing device 120 may include an acquisition module 402, a control module 404, a processing module 406, and a storage module 408. The processing device 120 may be implemented on various components. For example, at least a portion of the processing device 120 may be implemented on a computing device as illustrated in FIG. 2 or a mobile device as illustrated in FIG. 3.

The acquisition module 402 may acquire data. The acquisition module 402 may acquire the data from the scanner 110, or a storage device (e.g., the storage 130, the storage 220, the storage 390, the memory 360, the storage module 408, or the Ike, or a combination thereof). The data may include image data (e.g., raw data, projection data, images, etc.) relating to a subject, personalized data relating to a subject, data relating to one or more components of the PET imaging system (e.g., the scanner 110), etc. In some embodiments, the acquisition module 402 may transmit the acquired data to other modules or units of the processing device 120 for further processing or storage. For example, the acquired data may be transmitted to the storage module 408 for storage. As another example, the acquisition module 402 may transmit the data (e.g., projection data) to the processing module 406 to reconstruct an image.

The control module 404 may control operations of the acquisition module 402, the processing module 406, the storage module 408, or other components of the PET system 100 (e.g., the scanner 110 of the PET system 100) by, e.g., generating one or more control parameters. For example, the control module 404 may control the acquisition module 402 to acquire image data (e.g., raw data, images, etc.). As another example, the control module 404 may control the processing module 406 to process the image data (e.g., raw data, images, etc.) acquired by the acquisition module 402. As still another example, the control module 404 may control the processing module 406 to generate a correction profile. As a further example, the control module 404 may control the operation of the scanner 110. In some embodiments, the control module 404 may receive a real-time command or retrieve a predetermined command provided by, e.g., a user (e.g., a doctor) or the PET system 100 to control one or more operations of the acquisition module 402 and/or the processing module 406. For example, the control module 404 can adjust the processing module 406 to generate one or more correction profiles according to the real-time command and/or the predetermined command. In some embodiments, the control module 404 may communicate with one or more other modules of the processing device 120 for exchanging information and/or data.

The processing module 406 may process data and/or information provided by various modules of the processing device 120. In some embodiments, the processing module 406 may process scanning data relating to a subject acquired by the acquisition module 402, scanning data retrieved from the storage module 408, etc. For example, the processing module 406 may determine whether scanning data relating to a subject needs to be corrected based on the scanning data. As another example, the processing module 406 may determine a correction profile based on scanning data acquired by an imaging device (e.g., the scanner 110). In some embodiments, the processing module 406 may reconstruct an image based on projection data according to a reconstruction technique, generate a report including one or more images and/or other related information, and/or perform any other function for image reconstruction in accordance with various embodiments of the present disclosure.

The storage module 408 may store data, models, control parameters, processed data, or the like, or a combination thereof. In some embodiments, the storage module 408 may store one or more programs and/or instructions that may be executed by the processor(s) of the processing device 120 to perform exemplary methods described in this disclosure. For example, the storage module 408 may store program(s) and/or instruction(s) that can be executed by the processor(s) of the processing device 120 to acquire image data (e.g., projection data), reconstruct an image based on the image data, and/or display any intermediate result or a resultant image.

In some embodiments, one or more modules illustrated in FIG. 4 may be implemented in at least part of the exemplary PET system 100 as illustrated in FIG. 1. For example, the acquisition module 402, the control module 404, the processing module 406, and/or the storage module 408 may be integrated into a console (not shown). Via the console, a user may set parameters for scanning a subject, controlling imaging processes, controlling parameters for reconstruction of an image, viewing reconstructed images, etc. In some embodiments, the console may processing device 120 include an interface to exchange information with the terminal 140. In some embodiments, at least part of the console may be implemented on the terminal 140. For instance, a user interface of the console may be implemented on the terminal 140; through the user interface, a user may exchange information with the PET system 100, or a portion thereof, by way of, e.g., providing instructions, receiving results, viewing images, etc.

Figure 5:
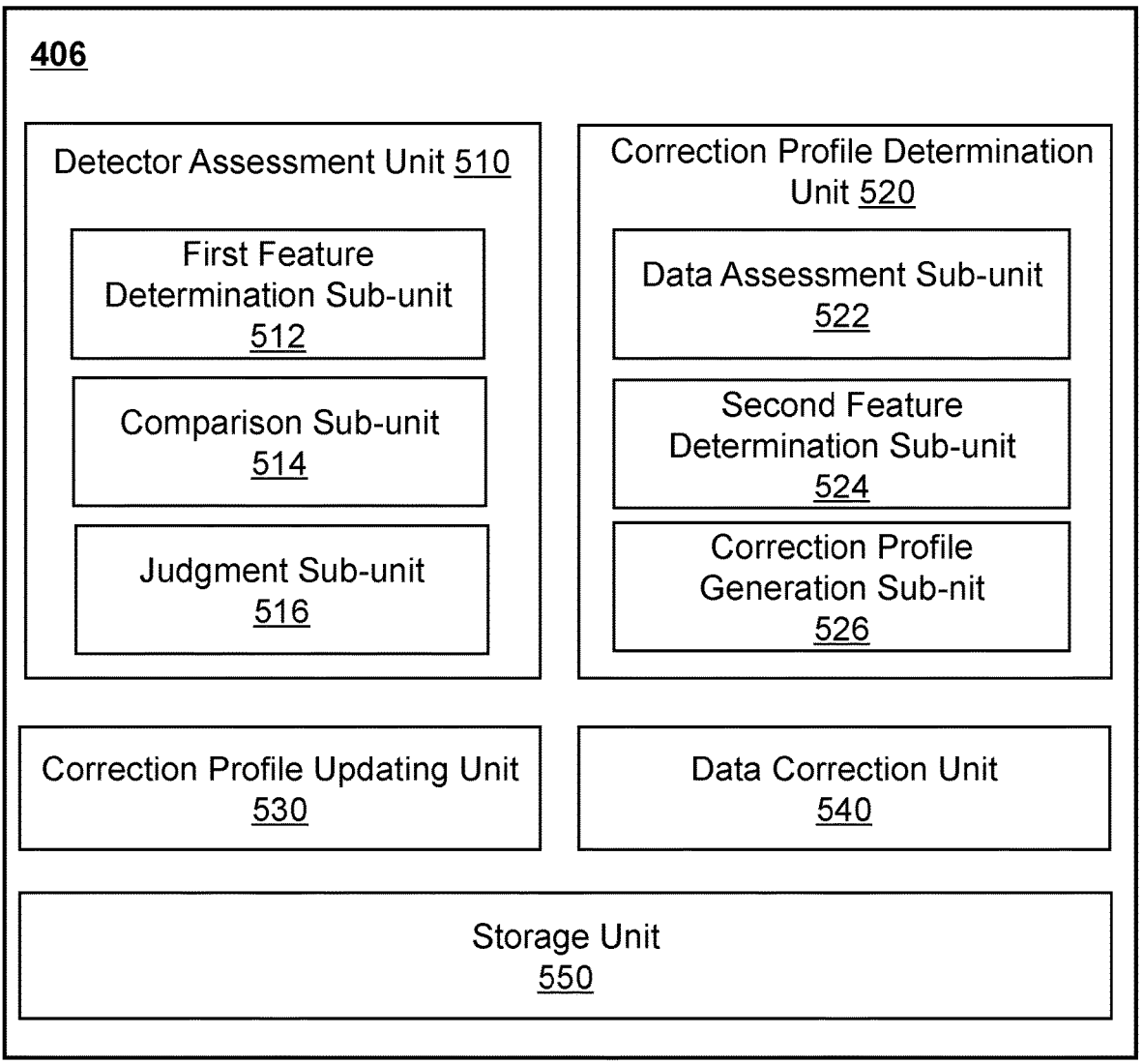
FIG. 5 is a block diagram illustrating an exemplary processing module according to some embodiments of the present disclosure.

FIG. 5 is a block diagram illustrating an exemplary processing module 406 according to some embodiments of the present disclosure. As shown, the processing module 406 may include a detector assessment unit 510, a correction profile determination unit 520, a correction profile updating unit 530, a data correction unit 540, and a storage unit 550. The processing module 406 may be implemented on various components (e.g., the processor 210 of the computing device 200 as illustrated in FIG. 2). For example, at least a portion of the processing module 406 may be implemented on a computing device as illustrated in FIG. 2 or a mobile device as illustrated in FIG. 3.

The detector assessment unit 510 may assess the performance of a detector (e.g., the detector 114) according to one or more conditions. In some embodiments, the detector may be assessed based on data relating to the detector. In some embodiments, the detector may be assed based on scanning data relating to a subject acquired by the detector. In some embodiments, the detector assessment unit 510 may transmit an assessment result of the detector to other units or blocks of the processing module 406 for further processing or storage. For example, the detector assessment unit 510 may transmit the assessment result of the detector to the correction profile determination unit 520. The correction profile determination unit 520 may determine whether the scanning data acquired by the detector needs a correction based on the assessment result of the detector.

In some embodiments, the detector assessment unit 510 may further include a first feature determination sub-unit 512, a comparison sub-unit 514, and a judgment unit 516. The first feature determination sub-unit 512 may determine feature data relating to scanning data acquired by the detector. The comparison sub-unit 514 may perform a comparison in a process for, for example, assessing the detector. For example, the comparison sub-unit 514 may compare the feature data with reference feature data to determine a difference between the two. The judgment sub-unit 516 may perform a judgment function in a process for, for example, assessing the detector. For example, the judgment sub-unit 516 may determine whether one or more conditions are satisfied. Merely by way of example, the judgment may be performed based on the features data from the first feature determination sub-unit 512 and/or the comparison results from the comparison sub-unit 514.

The correction profile determination unit 520 may determine a correction profile relating to a detector. In some embodiments, the correction profile determination unit 520 may determine source data for determining the correction profile according to one or more conditions. In some embodiments, the correction profile determination unit 520 may generate the correction profile based on the determined source data. In some embodiments, the correction profile determination unit 520 may transmit the correction profile relating to the detector to other units or blocks of the processing module 406 for further processing or storage. For example, the correction profile determination unit 520 may transmit the correction profile relating to the detector to the correction profile updating unit 530 for updating a system correction profile. As another example, the correction profile determination unit 520 may transmit the correction profile relating to the detector to the data correction unit 540 for correcting scanning data relating to a subject.

In some embodiments, the correction profile determination unit 520 may further include a data assessment sub-unit 522, a second feature determination sub-unit 524, and a correction profile generation sub-unit 526. The data assessment sub-unit 522 may determine source data for determining a correction profile by assessing scanning data relating to a subject. The second feature determination sub-unit 524 may determine feature data based on the determined source data. The correction profile generation sub-unit 526 may generate the correction profile based on the feature data.

The correction profile updating unit 530 may update at least one portion of a system correction profile based on a correction profile relating to a detector determined by, for example, the correction profile determination unit 520. In some embodiments, the correction profile updating unit 530 may transmit the updated system correction profile to other units or blocks of the processing module 406 for further processing or storage. For example, the correction profile updating unit 530 may transmit the updated system correction profile to the data correction unit 540 for correcting scanning data relating to a subject acquired by the detector. As another example, the correction profile updating unit 530 may transmit the updated system correction profile to the storage unit 550 for storage.

The data correction unit 540 may adjust scanning data based on a correction profile obtained from, for example, the correction profile determination unit 520, the correction profile updating unit 530, the storage unit 550, etc.

The storage unit 550 may store information including, for example, information for performing a correction relating to a component of an imaging device (e.g., a detector). The information may include programs, software, algorithms, data, text, number, and some other information. For example, the storage unit 550 may store a correction profile determined by the correction profile determination unit 520. In some embodiments, the storage unit 550 may store a condition, a criterion, a threshold, or a standard for assessing a detector. The storage unit 550 may store intermediate results and/or final results in the process for performing a correction relating to a component of an imaging device (e.g., a detector).

It should be noted that the above description of the processing module 430 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the correction profile determination unit 520 and the correction profile updating unit 530 may be integrated into one single unit. As another example, the detector assessment unit 510 and the correction profile determination unit 520 may be integrated into one single unit.

Figure 6:
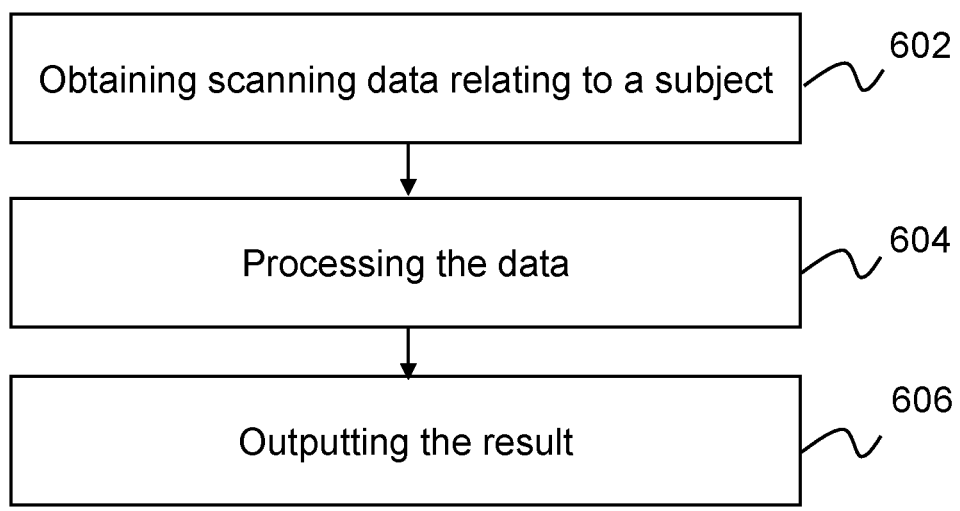
FIG. 6 is a flowchart illustrating an exemplary process for processing scanning data relating to a subject according to some embodiments of the present disclosure.

FIG. 6 is a flowchart illustrating an exemplary process 600 for processing scanning data relating to a subject according to some embodiments of the present disclosure. In some embodiments, one or more operations of process 600 illustrated in FIG. 6 may be implemented in the PET system 100 illustrated in FIG. 1. For example, the process 600 illustrated in FIG. 6 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3).

In 602, scanning data relating to a subject may be obtained. Operation 602 may be performed by the acquisition module 402. In some embodiments, the scanning data relating to the subject may include raw data. As used herein, the raw data may refer to data generated by the detector in response to detected photons emitted from a subject. Exemplary raw data may include an electrical signal (e.g., a scintillation signal), a digital signal, feature information, projection data (e.g., sinogram data), etc., as described in connection with FIG. 1. In some embodiments, the scanning data relating to the subject may be obtained from the scanner 110, the storage 130, the terminal 140, and/or an external data source. For example, the raw data relating to the subject may be obtained from the scanner 110 generated by the detector 114 corresponding to detected photons emitted from the subject being examined.

In 604, the scanning data relating to a subject may be processed. Operation 604 may be performed by the processing module 406. In some embodiments, at least a portion of the scanning data (e.g., the raw data, the information relating to the detector, etc.) relating to the subject may be assessed to determine whether the scanning data needs to be corrected, More descriptions for determining whether the scanning data needs to be corrected may be found elsewhere in the present disclosure. See, e.g., FIGS. 8, 9, and 13 and the description thereof. In some embodiments, at least a portion of the scanning data (e.g., the raw data) relating to the subject may be corrected based on a correction profile. More descriptions for determining a correction profile may be found elsewhere in the present disclosure. See, e.g., FIGS. 10 and 11. In some embodiments, an image relating to the subject may be reconstructed based on the corrected scanning data according to one or more reconstruction techniques. Exemplary reconstruction techniques may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof.

In 606, the result may be outputted. Operation 606 may be performed by the processing module 406. The result may include intermediate data generated in the scanning data processing. For example, the result may include the corrected scanning data relating to the subject. The corrected scanning data relating to the subject may be outputted to the storage 130 or other storages for storing. In some embodiments, the corrected scanning data may be stored for future use as reference data for determining whether scanning data relating to another subject need to be corrected. As another example, the result may include a correction profile. The correction profile may be outputted to the storage 130 for storing. In some embodiments, the result may include an image reconstructed based on the corrected scanning data relating to the subject. The image may be outputted to the terminal 140 for display.

It should be noted that the above description is merely provided for the purposes of illustration, and not intended to knit the scope of the present disclosure. For persons having ordinary skills in the art, multiple variations or modifications may be made under the teachings of the present disclosure. However, those variations and modifications do not depart from the scope of the present disclosure. For example, process 600 may include an operation for pre-processing the scanning data relating to the subject.

Figure 7:
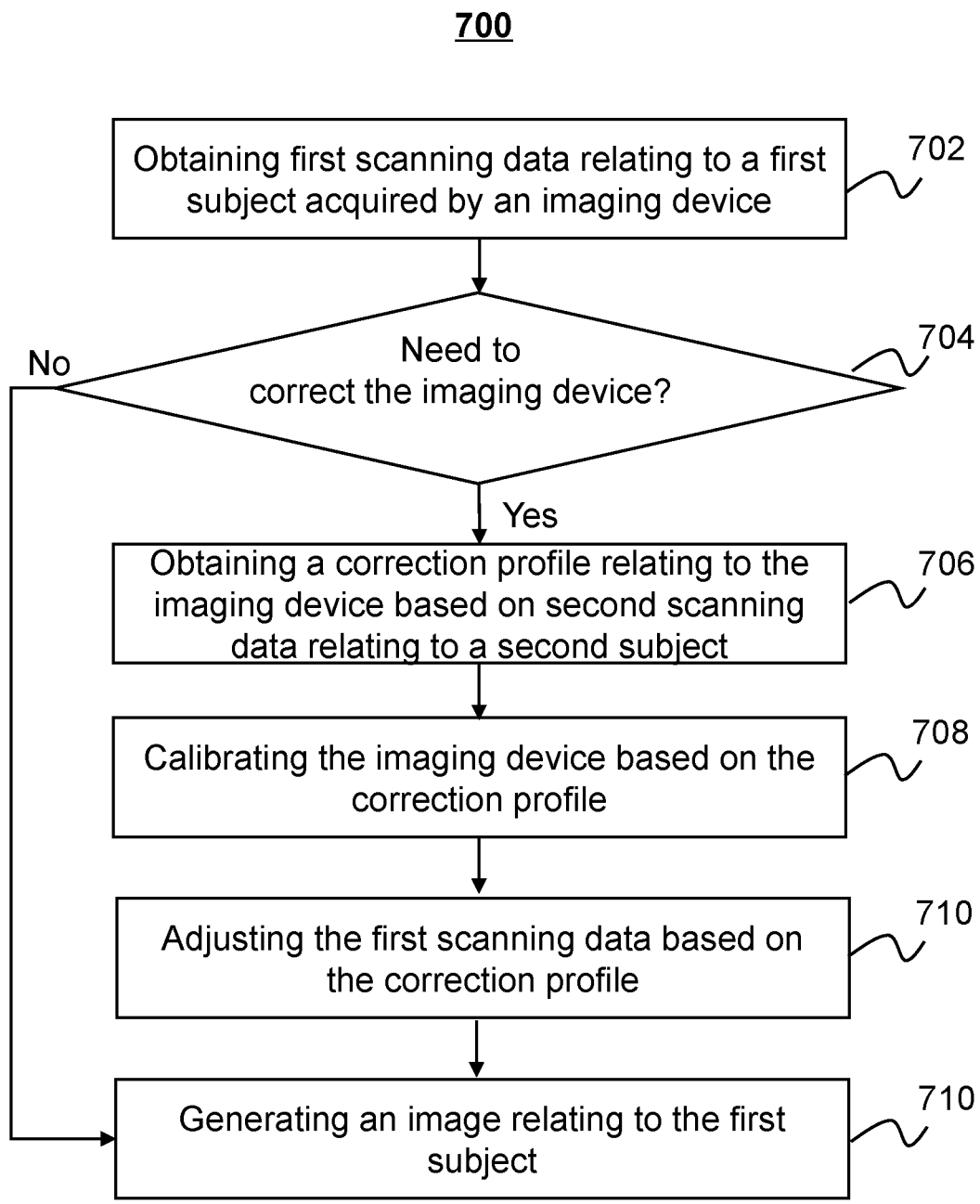
FIG. 7 is a flowchart illustrating an exemplary process for performing a correction relating to an imaging device according to some embodiments of the present disclosure.

FIG. 7 is a flowchart illustrating an exemplary process 700 for performing a correction relating to an imaging device according to some embodiments of the present disclosure. In some embodiments, one or more operations of process 700 illustrated in FIG. 7 may be implemented in the PET system 100 illustrated in FIG. 1. For example, the process 700 illustrated in FIG. 7 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Operation 604 as described in FIG. 6 may be performed according to process 700.

In 702, first scanning data relating to a first subject acquired by an imaging device may be obtained. Operation 702 may be performed by the acquisition module 402. In some embodiments, the imaging device (e.g., the scanner 110) may include, for example, a PET device, a PET-CT device, a PET-MRI device, etc. The imaging device may include a detector with multiple detector blocks as described in connection with FIG. 1, The first scanning data relating to the first subject may be acquired by the detector (e.g., the detector 114) corresponding to detected radiation events (e.g., radiation events in the form of photons) from the first subject. In some embodiments, the first scanning data may include raw data relating to the first subject.

In some embodiments, the first scanning data may include first feature information relating to radiation events. The first feature information relating to the radiation events may be used to determine coincidence events. The first feature information relating to the radiation events may include time information, energy information, and position information. The time information relating to a radiation event may refer to a time point when a radiation photon impinges on a detector (e.g., the detector 114) and/or a time offset of two radiation events detected by two detector blocks along a line of response (LOR). The energy information relating to a radiation event may refer to an energy intensity of a radiation photon impinging on the detector. The position information relating to a radiation event may refer to a position where a radiation photon impinges on a detector (e.g., the detector 114).

In 704, a determination may be made as to whether the imaging device needs to be corrected. Operation 704 may be performed by the detector assessment unit 504. If it is determined that the imaging device needs to be corrected, process 700 may proceed to 706. If it is determined that the imaging device does not need to be corrected, process 700 may proceed to 710.

In some embodiments, whether the imaging device needs to be corrected may be determined by assessing the imaging device based on feature data relating to the detector according to a condition. The feature data relating to the detector may be determined based on scanning data relating to a subject (e.g., the first scanning data relating to the first subject or second scanning data relating to a second subject different from the first subject.). For example, if the feature data relating to the detector corresponding to the first scanning data satisfies the condition, it may be determined that the imaging device needs to be corrected. If the feature data relating to the detector corresponding to the first scanning data does not satisfy the condition, it may be determined that the imaging device does not need to be corrected.

Exemplary feature data relating to the detector may include a response rate of a detector block, an energy distribution corresponding to a detector block, a position spectrum of a detector block, a time offset of two detector blocks corresponding to a line of response (LOR), or the like, or a combination thereof. The feature data relating to the detector and/or the condition may relate to a performance parameter of the imaging device. Exemplary performance parameters of the imaging device may include a sensitivity of the detector, an energy resolution of the detector, a time resolution of the detector, a spatial resolution of the detector, or the like, or a combination thereof. For example, a larger difference between an energy peak of an energy distribution corresponding to a detector block in the detector and a reference energy peak may suggest a lower energy resolution of the imaging device. As used herein, the efficiency of a detector block may be defined by a ratio of the number of signals (e.g., electrical signals or digital signals) generated in response to detected radiation photons (or referred to as a signal count) to the number of the detected or emitted photons (or referred to as a detected or emitted photon count) for a period of time. The efficiency of a detector block may be estimated based on a response time of the detector block. For example, the shorter the response time of the detector is, the higher the efficiency of the detector block may be.

In some embodiments, the feature data relating to the detector may be determined based on data relating to the imaging device. The data relating to the imaging device may include scanning data relating to a subject (e.g., the first scanning data relating to the first subject) and a set of data relating to the detector in the imaging device (e.g., statistic data of response rates relating to the detector blocks in the detector). For example, the feature data relating to the detector corresponding to the first scanning data may be determined based on the feature information relating to radiation events included in the first scanning data. Furthermore, the energy distribution corresponding to a detector block may be determined based on the energy information relating to radiation events detected by the detector block. More descriptions for determining whether the imaging device needs to be corrected may be found elsewhere in the present disclosure. See for example, FIGS. 8, 9, and 13 and the description thereof.

In 706, a correction profile relating to the imaging device may be obtained. In some embodiments, the correction profile relating to the imaging device may be determined based on the current status of the detector 114 reflected in the first scanning data and a target status of the detector 114. In some embodiments, the correction profile relating to the imaging device may be selected and retrieved from a library including a plurality of correction profiles. An entry of the library may include a status of the detector 114 and a correction profile corresponding to a deviation of the status of the detector 114 from its target status. A status of the detector 114 may be defined by one or more feature parameters described elsewhere in the present disclosure. For instance, a status of the detector 114 may be defined by one or more feature parameters with respect to energy performance, time performance, position performance, or the like, or a combination thereof, of the detector 114. The energy performance, the time performance, and the position performance may be represented by the energy resolution, the time resolution, and the spatial resolution of the detector, respectively, as described above. A deviation may include one or more aspects of the status of the detector 114 including, e.g., energy performance, time performance, position performance, or the like, or a combination thereof. The selection may be based on, e.g., the current status of the detector 114 reflected in the first scanning data.

In some embodiments, a plurality of options for obtaining the correction profile may be provided. For instance, the library is searched and a correction profile may be retrieved from the library if the current status defined by one or more feature parameters of the detector 114 matches an entry in the library. As another example, if no perfect match of the current status of the detector 114 is found with respect to the entries available in the library, one or more correction profiles with similar status compared to the current status of the detector 114 may be retrieved, and the correction profile may be generated based on the retrieved one or more correction profiles by way of, e.g., extrapolation or interpolation. As a further example, a correction profile may be generated based on the current status of the detector 114 reflected in the first scanning data. Operation 706 may be performed by the acquisition module 402. The correction profile may be determined by the correction profile determination unit 506.

Figure 10:
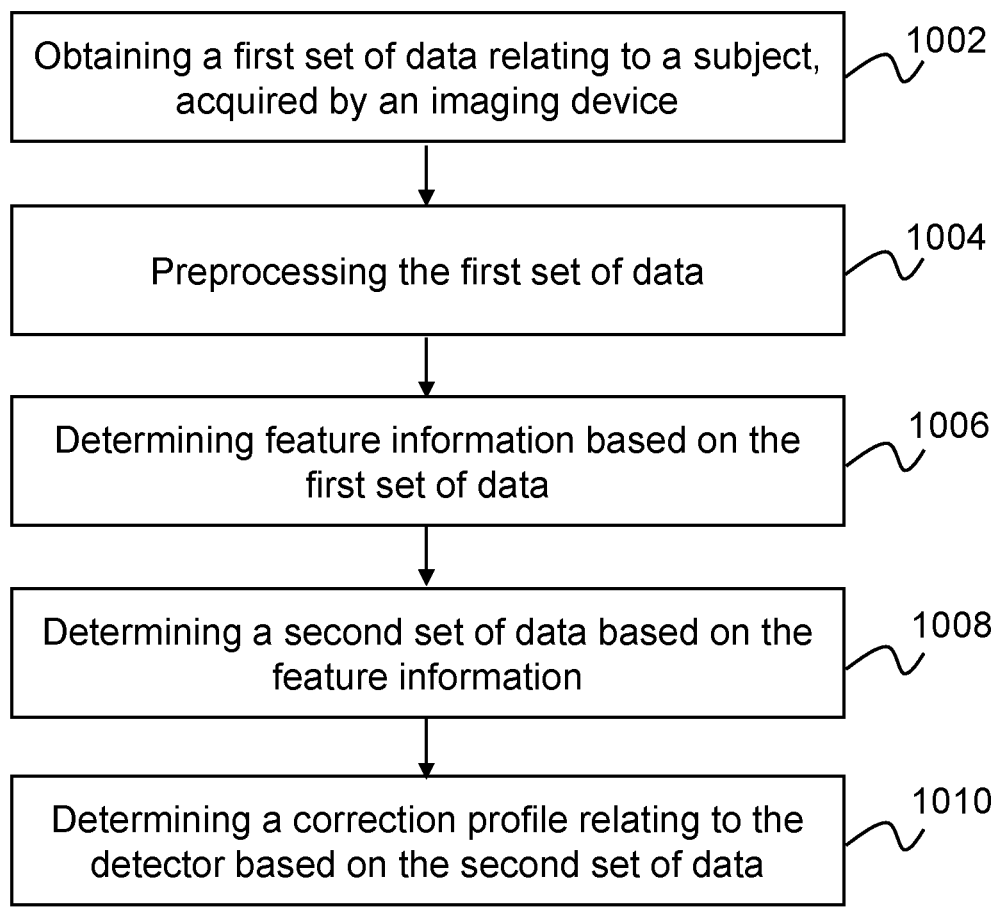
FIG. 10 is a flowchart illustrating an exemplary process for determining a correction profile based on scanning data relating to a subject according to some embodiments of the present disclosure.
Figure 11:
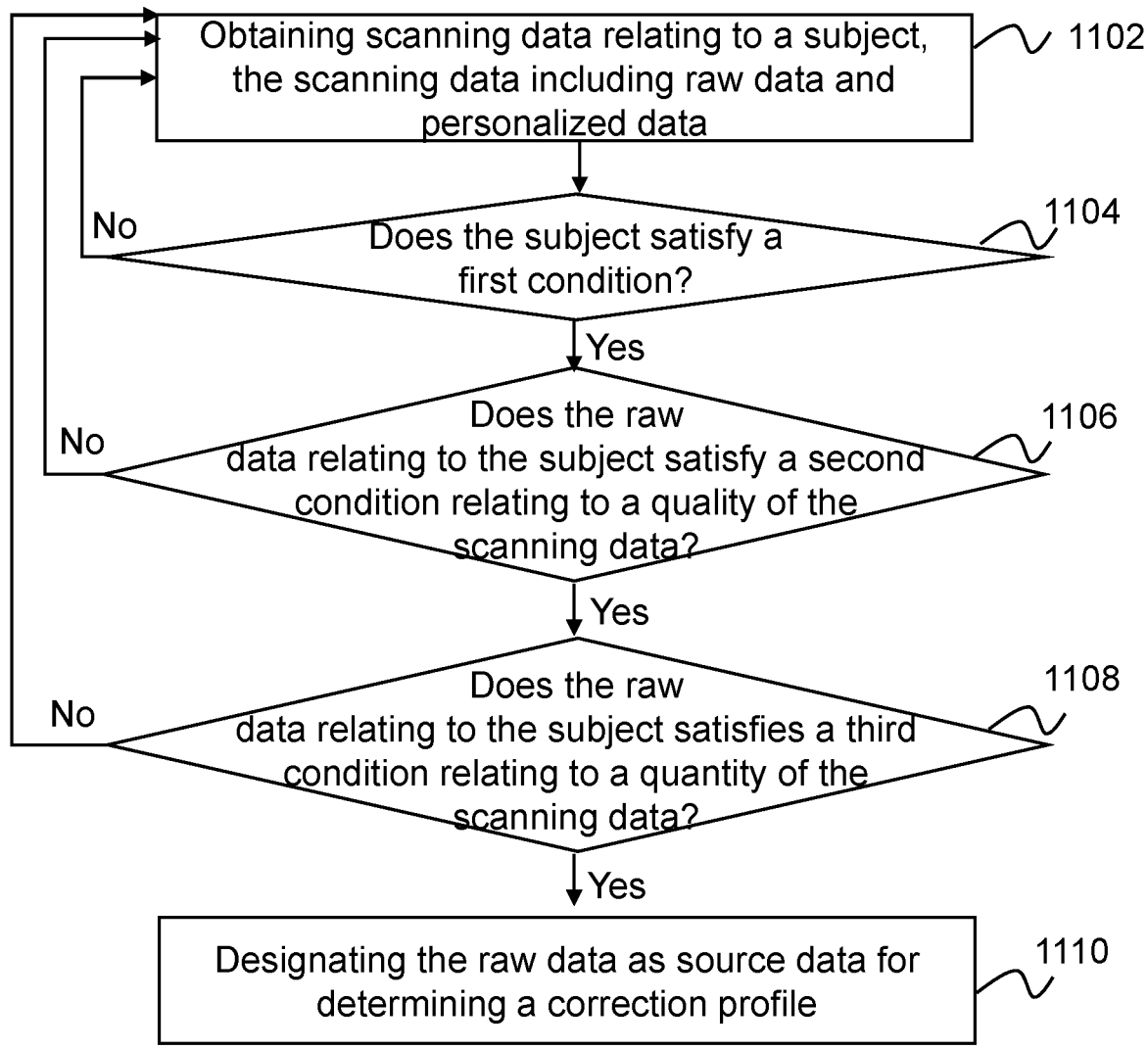
FIG. 11 is a flowchart illustrating an exemplary process for determining source data for determining a correction profile according to some embodiments of the present disclosure.

In some embodiments, a target status of the detector may be preset by, e.g., the manufacturer of the detector 114 or the scanner 110. In some embodiments, a target status of the detector 114 may be extracted from second scanning data relating to a second subject that is different from the first subject. The second scanning data relating to the second subject may be obtained from the scanner 110, the storage 130, the terminal 140, and/or other storages. For example, the second scanning data may be obtained from the storage 130 acquired by the scanner 110 corresponding to detected radiation events from the second subject. In some embodiments, the second subject and/or the second scanning data relating to the second subject may be assessed based on one or more conditions according to process 1100 as illustrated in FIG. 11. The second scanning data relating to the second subject may include second feature information relating to radiation events. Merely by way of example, the correction profile may be determined based on the second feature information relating to radiation events included in the second scanning data according to process 10 as illustrated in FIG. 10. In some embodiments, a correction profile used to correct scanning data of a subject under examination may be determined based on scanning data of a group of one or more subjects including the subject under examination or not. In some embodiments, a correction profile used to correct scanning data of a subject under examination may be determined based on prior scanning data of the same subjects.

The correction profile may be used to correct the first scanning data relating to the first subject. Furthermore, the correction profile may be used to correct the first feature information relating to radiation events included in the first scanning data. The correction profile for correcting the first feature information may be determined based on the second feature information corresponding to the first feature information. For example, the correction profile for correcting the energy information included in the first scanning data may be determined based on the energy information included in the second scanning data.

In some embodiments, the correction profile may include a plurality of correction coefficients. Each of the plurality of correction coefficients may correspond to at least one detector block. For example, if the correction profile is used to correct energy information relating to radiation events included in the first scanning data, a correction coefficient may correspond to an individual detector block. The energy intensities of radiation events detected by the detector block may be corrected by the correction coefficient corresponding to the detector block. As another example, if the correction profile is used to correct a time offset corresponding to two detector blocks corresponding to a line of response (LOR), a correction coefficient may correspond to two detector blocks (or an LOR), The time offsets of radiation events detected by the two detector blocks may be corrected by the correction coefficient corresponding to the two detector blocks.

The first condition may relate to personalized data relating to the second subject. The personalized data may include static data, dynamic data, or both. Exemplary static data may include various information regarding a subject including gender, age, birthday, a health history (for example, whether a subject has smoked before, information regarding a prior surgery, a food allergy, a drug allergy, a medical treatment history, a history of a genetic disease, a family health history, or the like, or a combination thereof), or the like, or a combination thereof. Exemplary dynamic data may include a current health condition of a subject, medications the second subject is taking, a medical treatment the subject is undertaking, diet, weight, height, or the like, or a combination thereof. In some embodiments, the second scanning data relating to the second subject for determining the correction profile may be assessed based on one or more second conditions. The second conditions may relate to, for example, the quantity of the second scanning data, a quality of the second scanning data, or the like, or a combination thereof. As used herein, the quantity of the second scanning data may represented by the number of radiation events (also referred to as a radiation event count) corresponding to the second scanning data. The quality of the second scanning data may be represented by the number of true coincidence events (also referred to as a true coincidence event count) corresponding to the second scanning data. In some embodiments, the quality of the second scanning data may be evaluated based on, for example, a noise equivalent counts ratio of the second scanning data. The greater the noise equivalent counts ratio is, the higher the quality of the second scanning data may be. The noise equivalent counts ratio may relate to, for example a count of true coincidence events, a count of scatter coincidence events, a count of random coincidence events, etc. The greater the count of true coincidence events, the smaller the count of scatter coincidence events and/or the count of random coincidence events are, the greater the noise equivalent counts ratio may be. In some embodiments, the quality of the second scanning data may be evaluated by, for example, assessing an image reconstructed based on the second scanning data. The image reconstructed based on the second scanning data may be evaluated by applying an image quality evaluation algorithm. Exemplary image quality evaluation algorithms may include MSE/PSNR image quality evaluation algorithms, a reduce-reference image quality evaluation algorithms, etc.

In 708, the imaging device may be calibrated based on the correction profile a system correction profile may be updated based on the correction profile. Operation 708 may be performed by the correction profile updating unit 530. In some embodiments, the imaging device may be calibrated via updating a system correction profile. In some embodiments, the system correction profile may include one or more correction files. A correction file may include a plurality of correction coefficients. A correction file may correspond to one of various correction relating to the PET system 100. Exemplary corrections relating to the PET system 100 may include an energy correction, a time correction, a position correction, or the like, or a combination thereof. The system correction profile may be stored in the terminal 140, the storage 130, and/or any other storage.

In some embodiments, at least one portion of the system correction profile may be updated based on the correction profile. For example, one or more of the correction files may be updated based on the correction profile. As another example, at least one portion of the plurality of correction coefficients in the system correction profile may be replaced by the corresponding correction coefficients in the correction profile, More descriptions for updating the system correction profile may be found elsewhere in the present disclosure. See, e.g., FIG. 12 and FIG. 16 and the description thereof.

In 710, the first scanning data may be adjusted based on the system correction profile. Operation 710 may be performed by the data correction profile 508. The first scanning data may be corrected by the plurality of first correction coefficients in the correction profile. Furthermore, the first feature information (e.g., the energy information, the time information, the position information, etc.) included in the first scanning data may be corrected by the plurality of first correction coefficients. Each of the plurality of first correction coefficients in the correction profile may correspond to at least one detector block in the imaging device. The first feature information relating to radiation events detected by a detector block may be corrected by a first correction coefficient corresponding to the detector block. For example, energy information relating to radiation events may include energy values of the radiation events detected by a detector block. The detector block may correspond to a correction coefficient in the correction profile. The energy values of the radiation events detected by the detector block may be corrected by multiplying the energy values with the correction coefficient.

In 712, an image may be generated. In some embodiments, the image may be generated based on the adjusted first scanning data determined in 710. In some embodiments, the image may be generated based on the first scanning data obtained in 702 if it is determined that the first scanning data so obtained does not need to be corrected.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 706 and 708 may be performed simultaneously. As another example. Operation 702 may be performed after operation 708, and 710 may be unnecessary. Further, the first scanning data relating to the first subject may be acquired by the imaging device based on the correction profile. In some embodiments, operation 710 may be omitted, and third scanning data may be obtained based on the system correction profile. The third scanning data may relate to a third subject same as or different from the first subject or the second subject.

Figure 8:
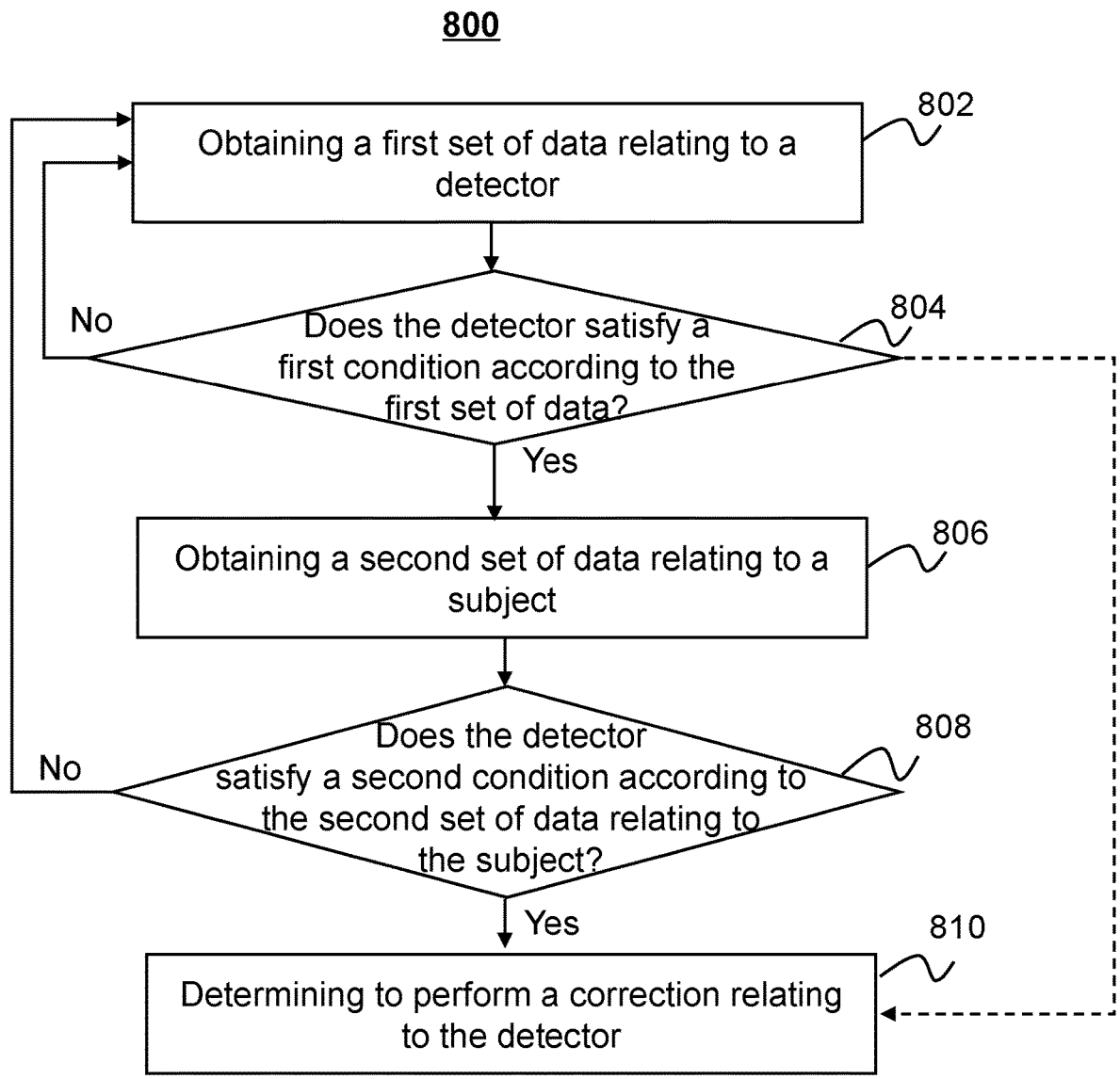
FIG. 8 is a flowchart illustrating an exemplary process for determining whether a correction relating to an imaging device needs to be performed according to some embodiments of the present disclosure.

FIG. 8 is a flowchart illustrating an exemplary process 800 for determining whether a correction relating to an imaging device needs to be performed according to some embodiments of the present disclosure. In some embodiments, one or more operations of process 800 illustrated in FIG. 8 may be implemented in the PET system 100 illustrated in FIG. 1. For example, the process 800 illustrated in FIG. 8 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Operation 704 as described in FIG. 7 may be performed according to process 800.

In 802, a first set of data relating to a detector may be obtained. Operation 802 may be performed by the acquisition module 402. In some embodiments, the detector may include multiple detector blocks. Each of the detector blocks may include at least one crystal and/or at least one photomultiplier as described in connection with FIG. 1. Each of the detector blocks may receive radiation photons emitted from a subject and generate electrical signals (e.g., scintillation pulses) or digital signals (i.e., data relating to radiation events) in response to the detected photons.

The first set of data relating to the detector may relate to a first feature parameter of the detector. Exemplary first feature parameters of the detector may include a response time of a detector block, an equivalent noise power of the detector, a linearity of a detector block, a dynamic range of a detector block, a quantum efficiency, etc. The detector blocks of the detector may be assigned to a first group or a second group. Detector blocks in the first group may be determined from the detector blocks of the detector manually or automatically. The detector block count of detector blocks in the first group may be set by a user via the terminal 140 or according to a default setting of the PET system 100. The second group may be determined based on the first feature parameter of the detector. Furthermore, a detector block having a first feature not satisfying a reference value may be assigned to the second group.

In some embodiments, the first set of data relating to the detector may include statistic data relating to one or more first feature parameters (e.g., response time) of the first group of detector blocks in the detector within a certain period of time. The number of detector blocks (or referred to as a detector block count) of the first group may be equal to or less than a total number of detector blocks (or referred to as a total detector block count) in the detector. In some embodiments, the detector block count of the first group may be set by a user via the terminal 140 or according to a default setting of the PET system 100.

In 804, a determination may be made as to whether the detector satisfies a first condition according to the first set of data, Operation 802 may be performed by the detector assessment unit 504. If the detector satisfies the first condition, process 800 may proceed to operation 806 or operation 810. If the detector does not satisfy the first condition, process 800 may proceed to operation 802. In some embodiments, the first condition may relate to the second group of detector blocks. The second group of detector blocks may be determined based on the first set of data relating to the detector. Furthermore, the second group of detector blocks may be determined based on the first group of detector blocks and one or more first feature parameters relating to the first group of detector blocks. For example, if one or more first feature parameters of a detector block in the first group does not satisfy a reference value or range, the detector block may be assigned to the second group. Furthermore, a detector block in the second group may have a first feature parameter (e.g., response rate) with a value lower than a reference value or beyond a reference range. The reference value or range may be set by a user via the terminal 140 or according to a default setting of the PET imaging system. For example, the reference value or range may be set by a user according to a factory setting of the imaging device.

In some embodiments, the first condition may include a first threshold (e.g., a constant) corresponding to a detector block count of the second group (or a ratio of the detector block count of the second group to the detector block count of the first group). If the detector block count of the second group (or the ratio of the detector block count of the second group to the detector block count of the first group) exceeds the first threshold (e.g., a constant), the detector may be considered satisfying the first condition, indicating that the status of the detector is abnormal. If the detector block count of the second group (or the ratio of the detector block count of the first group to the detector block count of the second group) is lower than or equal to the first threshold (e.g., a constant), the detector may be considered not satisfying the first condition, indicating that the status of the detector is normal.

In some embodiments, the first condition may include a first range corresponding to the detector block count of the second group (or the ratio of the detector block count of the second group to the detector block count of the first group). If the detector block count of the second group (or the ratio of the detector block count of the second group to the detector block count of the first group) is within the first range, the detector may satisfy the first condition, indicating that the status of the detector is abnormal. If the detector block count of the second group (or the ratio of the detector block count of the second group to the detector block count of the first group) is outside the first range, the detector may be considered not satisfying the first condition, indicating that the status of the detector is normal. In some embodiments, the first threshold and the first range may be set by a user or according to a default setting of the PET system 100.

In 806, a second set of data relating to a subject may be obtained. Operation 806 may be performed by the acquisition module 402. In some embodiments, the second set of data relating to the subject may be obtained from the scanner 110, the storage 130, the terminal 140, and/or any other storage. For example, the second set of data relating to the subject may be obtained from the scanner 110 acquired by the detector 114 corresponding to detected radiation photons emitted from the subject.

In some embodiments, the second set of data relating to the subject may include scanning data relating to the subject. For example, the scanning data relating to the subject may include raw data (e.g., digital signals) relating to radiation events. The second set of data relating to the subject may include feature information relating to the radiation events. The feature information relating to the radiation events may be determined by, for example, the electronics module 116 in the detector 114. Exemplary feature information may include energy information relating to the radiation events, position information relating to the radiation event, time information relating to the radiation events, etc., as described elsewhere in the present disclosure, See, for example, FIG. 7 and description thereof.

In 808, a determination may be made as to whether the detector satisfies a second condition according to the second set of data. Operation 808 may be performed by the detector assessment unit 504. If the detector satisfies the second condition, process 800 may proceed to operation 810. If the detector does not satisfy the second condition, process 800 may proceed to operation 802. In some embodiments, the second condition may relate to a second feature parameter relating to the detector blocks in the detector. The second feature parameter relating to the detector blocks in the detector may be determined based on the feature information included in the second set of data relating to the subject, Exemplary second feature parameters relating to the detector blocks in the detector may include an energy peak corresponding to a detector block, an offset of an LOR corresponding to two detector blocks located along the LOR, a position of a detector block corresponding to a radiation event, etc. As used herein, an energy peak corresponding to a detector block may refer to an energy value corresponding to a maximum count of radiation events detected by the detector block. A position of a radiation event corresponding to a detector block may refer to a two-dimensional position of the detector block detecting the radiation event. An offset of an LOR corresponding to two detector blocks may equal to a negative of a time of flight (TOF) bias between two radiation events corresponding to a coincidence event on the LOR. The second feature parameter relating to the detector blocks may indicate a performance parameter of the imaging device as described elsewhere in the present disclosure. For example, drifts of energy peaks corresponding to detector blocks may decrease an energy resolution of the imaging device. As another example, drifts of offsets of LORs may decrease a time resolution of the imaging device. As still an example, drifts of positions of detector blocks in the detector may decrease a spatial resolution of the imaging device.

In some embodiments, the second condition may relate to a difference between a second feature parameter relating to the detector blocks and a reference parameter. In some embodiments, the second condition may include a second threshold (e.g., a constant) corresponding to the difference between the second feature parameter relating to the detector blocks and the reference parameter. If the difference between the second feature parameter relating to the detector blocks and the reference parameter exceeds the second threshold (e.g., a constant), the detector may be considered satisfying the second condition, indicating that the status of the detector is abnormal. If the difference between the second feature parameter relating to the detector blocks and the reference parameter is lower than or equal to the second threshold (e.g., a constant), the detector may be considered not satisfying the second condition, indicating that the status of the detector is normal.

In some embodiments, the second condition may include a second range corresponding to the difference between the second feature parameter relating to the detector blocks and the reference parameter. If the difference between the second feature parameter relating to the detector blocks and the reference parameter is outside the second range, the detector may be considered satisfying the second condition, indicating that the status of the detector is abnormal. If the difference between the second feature parameter relating to the detector blocks and the reference parameter is within the second range, the detector may be considered not satisfying the second condition, indicating that the status of the detector is normal. In some embodiments, the reference parameter, the second threshold, and/or the second range may be set by a user or according to a default setting of the PET system 100.

In 810, a determination may be made as to perform a correction relating to the detector, Operation 810 may be performed by the detector assessment unit 504. In some embodiments, the correction relating to the detector may include correcting or adjusting scanning data relating to a subject (e.g., the second set of data relating to the second subject). More descriptions for determining a correction profile may be found elsewhere in the present disclosure. See, e.g., FIG. 10 and the description thereof.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or both of operations 802 and 804 may be omitted. As another example, one or more of operations 806, 808 and 810 may be omitted. In some embodiments, process 800 may further include outputting one or more notifications. The notifications may be used to, for example, remind a user the correction relating to the detector may need to be performed or the correction relating to the detector may need not to be performed.

Figure 9:
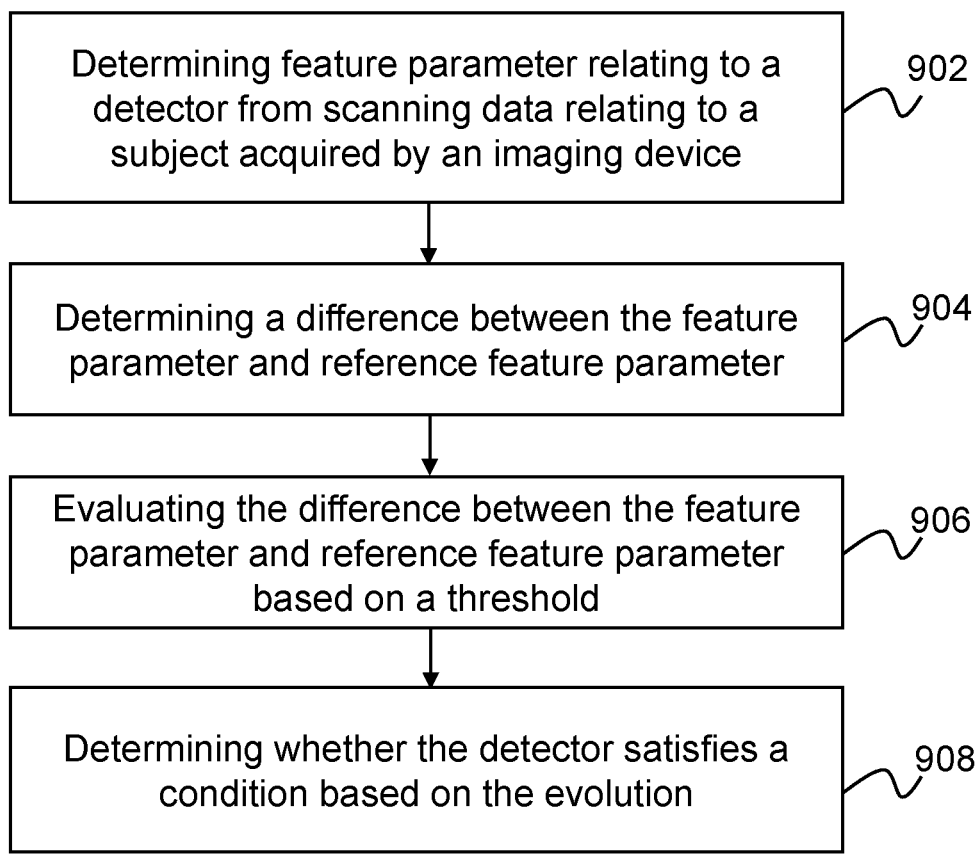
FIG. 9 is a flowchart illustrating an exemplary process for assessing a detector based on scanning data relating to a subject according to some embodiments of the present disclosure.

FIG. 9 is a flowchart illustrating an exemplary process 900 for assessing a detector based on scanning data relating to a subject according to some embodiments of the present disclosure. In some embodiments, one or more operations of process 900 illustrated in FIG. 9 may be implemented in the PET system 100 illustrated in FIG. 1, For example, the process 900 illustrated in FIG. 9 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Operation 808 as described in FIG. 8 may be performed according to process 900.

In 902, a feature parameter may be extracted from scanning data relating to a subject acquired by an imaging device including a detector. Operation 902 may be performed by the first feature determination unit 512. The detector (e.g., the detector 114) may include multiple detector blocks. A detector block may include at least one crystal. More descriptions for the detector may be found elsewhere in the present disclosure. See, e.g., FIG. 1 and the description thereof. The scanning data relating to the subject may relate to radiation events and feature information relating to the radiation events as described in connection with operation 806. The feature information included in the scanning data may include energy information relating to the radiation events, position information relating to the radiation events, time information relating to the radiation events, etc., as described elsewhere in the present disclosure. See, for example, FIG. 8 and description thereof. The feature parameter may include an energy peak corresponding to a detector block, an offset of an LOR corresponding to two detector blocks located along the LOR, positions of detector blocks detecting radiation events, etc., as described in connection with operation 806.

In some embodiments, the feature parameter relating to the detector may be determined based on the feature information relating to radiation events detected by the detector. For example, the energy information relating to radiation events detected by a detector may include a statistic data of energy values relating to the radiation events detected by the detector. In some embodiments, the statistical data of energy values relating to radiation events may be represented by an energy distribution corresponding to a crystal or detector block. An energy distribution corresponding to a crystal or detector block may represent a relationship between an energy value and a radiation event count. An energy value may correspond to a radiation event count. As another example, the position information relating to the radiation events may include multiple position spectrums relating to respective crystals in each of the multiple detector blocks in the detector. A position spectrum corresponding to a detector block may denote positions of crystals in the detector block, Positions of the detector blocks in the detector may be determined based on multiple position spectrums corresponding to the multiple detector blocks. In some embodiments, the positions of the detector blocks in the detector may be represented by two-dimensional (2D) planar positions (e.g., a 2D map). The 2D planar positions of the detector blocks in the detector may correspond to third-dimensional (3D) spatial positions of the detector blocks in the detector. The 3D spatial position of a detector block in the detector may correspond to the positon of the detector block arranged relative to the other detector blocks and/or a component of the imaging device (e.g., the gantry 112) in space. The two-dimensional (2D) planar position of a detector block may be represented by a position spectrum relating to crystals in the detector block. The 3D spatial position of the detector block in the detector may have a relationship with the two-dimensional (2D) planar position of the detector block. In some embodiments, if a detector is normal, the 2D planar positions of the detector blocks in the detector may have a linear relationship with the 3D spatial positions of the detector blocks in the detector. If the detector is abnormal, the 2D planar positions of the detector blocks in the detector may have a non-linear relationship with the 3D spatial positions of the detector blocks in the detector.

In 904, a difference between the feature parameter and reference feature parameter may be determined. Operation 904 may be performed by the comparison sub-unit 514. In some embodiments, the reference feature parameter may include one or more desired values corresponding to the feature parameter (e.g., an energy peak corresponding to a detector block, the 2D planar positions of the detector blocks, an offset of an LOR), etc. In some embodiments, the reference feature parameter (e.g., desired values) may be determined based on a most recent correction relating to the detector the PET system 100 has performed that may reflect the capacity or efficiency of the system correction profile currently available to correct scanning data acquired by the PET system 100. In some embodiments, the reference feature parameter may be set by a user via the terminal 140 or according to a default setting of the PET system 100.

In 906, the difference between the feature parameter and the reference feature parameter may be evaluated based on, e.g., a threshold. Operation 906 may be performed by the detector assessment unit 504. In some embodiments, the threshold (e.g., a constant) may be set by a user via the terminal 140 or according to a default setting of the PET system 100. In some embodiments, the difference between the feature parameter relating to the detector and reference feature parameter may be represented by a drift distribution of the feature parameter corresponding to the detector blocks in the detector. The drift distribution of the feature parameter may indicate a relationship between a drift value of the feature parameter and a detector block count. For example, a drift distribution of energy peaks corresponding to the detector blocks may indicate a relationship between a drift value of energy peak and a detector block count having the drift value of energy peak. In some embodiments, the difference between the feature parameter relating to the detector and reference feature parameter may be represented by a coefficient relating to the drift distribution of the feature parameter. The coefficient relating to the drift distribution may include a mean value relating to the drift distribution, a standard deviation relating to the drift distribution, an integral value relating to the drift distribution within an interval, or the like, or a combination thereof.

In some embodiments, the evaluation of the difference between the feature parameter relating to the detector and the reference feature parameter based on the threshold may include comparing the coefficient of the drift distribution and the threshold.

In 908, a determination may be made as to whether the imaging device satisfies a condition based on the evaluation. Operation 908 may be performed by the judgment sub-unit 516. In some embodiments, the condition may relate to a performance parameter of the imaging device, such as a sensitivity of the detector, an energy resolution of the imaging device, a time resolution of the detector, a spatial resolution of the detector, etc., as described elsewhere in the present disclosure. For example, the imaging device may be considered abnormal if the performance parameter of the imaging device satisfies the condition. In some embodiments, if the difference between the feature parameter and the reference feature parameter satisfies the threshold, the imaging device may be considered abnormal. If the difference between the feature parameter and the reference feature parameter does not satisfy the threshold, the imaging device may be considered normal. Furthermore, the difference between the feature parameter and the reference feature parameter may be considered satisfying the threshold if the coefficient relating to the drift distribution of the feature parameter exceeds the threshold. The difference between the feature parameter and the reference feature parameter may be considered not satisfying the threshold if the coefficient relating to the drift distribution of the feature parameter is lower than or equal to the threshold.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 906 and 908 may be performed simultaneously.

FIG. 10 is a flowchart illustrating an exemplary process 1000 for determining a correction profile based on scanning data relating to a subject according to some embodiments of the present disclosure. In some embodiments, one or more operations of process 1000 illustrated in FIG. 10 may be implemented in the PET system 100 illustrated in FIG. 1. For example, the process 1000 illustrated in FIG. 10 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Operation 706 as described in FIG. 7 may be performed according to process 1000.

In 1002, a first set of data relating to a subject acquired by an imaging device may be obtained. Operation 1002 may be performed by the acquisition module 402. The imaging device (e.g., the scanner 110) may include a detector (e.g., the detector 114). The detector (e.g., the detector 114) may include multiple detector blocks. Each of the detector blocks may include at least one crystal as described elsewhere in the present disclosure. See, for example, FIG. 1 and the descriptions thereof.

The first set of data may include raw data (e.g., electrical signals, digital signals, projection data, etc.) relating to the subject. For example, the first set of data may include multiple electrical signals (e.g., scintillation pulses). The multiple electrical signals (e.g., scintillation pulses) may be generated by the multiple detector blocks in response to detected radiation photons (e.g., gamma photons) emitted from the subject. In some embodiments, the first set of data relating to the subject may include digital signals (e.g., data relating to radiation events). The digital signals may be generated by, for example, the electronics module 116 by processing the electrical signals (e.g., scintillation pulses). In some embodiments, the first set of data relating to the subject may include projection data relating to the subject. The projection data (e.g., sinogram data) relating to the subject may be generated by, for example, the electronics module 116 by processing the digital signals. In some embodiments, the first set of data relating to the subject may include physiological data (e.g., an ECG signal, a respiration signal, etc.) relating to the subject. The physiological data and the raw data relating to the subject may be acquired at the same time. In some embodiments, the first set of data may be assessed based on one or more conditions as described in connection with FIG. 11.

In 1004, the first set of data may be preprocessed. Operation 1004 may be performed by the data assessment sub-unit 522. In some embodiments, the first set of data may include, for example, noise, data relating to motions of at least part of the subject (e.g., respiratory motion, cardiac motion, hemokinesis, etc.), a physiological signal (e.g., an ECG signal, a respiration signal, etc.), etc. The preprocessing of the first set of data may be used to remove or reduce, for example, the noise, the data relating to motions of at least one part of the subject (e.g., respiratory motion, cardiac motion, hemokinesis, etc.), the physiological signal (e.g., an ECG signal, a respiration signal, etc.), etc., from the first set of data.

In some embodiments, the noises included in the first set of data may be removed based on a denoising technique. Exemplary denoising techniques may include a spatial-domain filter algorithm, a transform-domain filter algorithm, a morphological noise filter algorithm, or the like, or a combination thereof. Exemplary spatial-domain filter algorithms may include a field average filter algorithm, a median filter algorithm, a Gaussian filter algorithm, or the like, or a combination thereof. Exemplary transform-domain filter algorithms may include a Fourier transform algorithm, a Walsh-Hadamard transform algorithm, a cosine transform algorithm, a K-L transform algorithm, a wavelet transform algorithm, or the like, or a combination thereof.

In some embodiments, the data relating to motions of at least part of the subject may be removed from the first set of data based on a retrospective gating technique (e.g., an ECG retrospective gating technique). According to the retrospective gating technique, the first set of data may be processed based on a physiological signal (e.g., an ECG signal, a respiration signal, etc.). In some embodiments, the physiological signal and the first set of data relating to the subject may be acquired synchronously. In some embodiments, motion information may be obtained by analyzing the first set of data itself. For instance, PET data may include information regarding respiratory motion, cardiac motion, or the like, or a combination thereof. Information of a motion may include, e.g., the motion frequency, the motion amplitude, etc., of the subject over time. Then, data relating to a motion of at least part of the subject may be removed from the first set of data according to the motion information and time information represented in, e.g., the physiological signal, the first set of data itself, or the like, or a combination thereof.

Merely by way of example, the first set of data includes a first sub-set of data and a second sub-set of data. The first sub-set of data may be used in determining a correction profile relating to the imaging device as described elsewhere in the present disclosure. The second sub-set of data may be determined by excluding the first sub-set of data from the first set of data. The first set of data may be preprocessed by removing the second sub-set of data from the first set of data.

In 1006, feature information may be determined based on the first set of data (with or without the preprocessing). Operation 1006 may be performed by the second feature determination sub-unit 524. In some embodiments, the first set of data may include the feature information (e.g., energy information, position information, time information, etc.) relating to radiation events detected by the detector as described elsewhere in the present disclosure. See, for example, FIGS. 7 through 10 and descriptions thereof. In some embodiments, the feature information may be extracted from the first set of data based on a feature extraction technique. Exemplary feature extraction techniques for extracting energy information relating to radiation events may include a peak detection and hold algorithm, a gated integration algorithm, a digital sampling integration algorithm, a multi-voltage threshold (MVT) algorithm, or the like, or a combination thereof. Exemplary feature extraction techniques for extracting position information relating to radiation events may include a value integration algorithm, a barycenter algorithm, or the like, or a combination thereof. Exemplary feature extraction techniques for extracting position information relating to radiation events may include applying a leading-edge discriminator (LED), a constant fraction discriminator (CFD), an ADC sampling algorithm, a mean PMT pulse model, a multi-voltage threshold algorithm, etc.

In 1008, a second set of data may be determined based on the feature information. Operation 1008 may be performed by the data assessment sub-unit 522. The second set of data may correspond to the feature information determined in 1006. For example, if the feature information determined in 1006 includes energy information relating to radiation events, the second set of data may include multiple groups of single events and energy values corresponding to each of the single events. A group of single events may correspond to a detector block that has detected the group of single events. As another example, if the feature data determined in 1006 includes position information relating to radiation events corresponding to the detector blocks, the second set of data may include multiple groups of look up tables (LUTs) relating to the detector blocks. A group of the LUTs may correspond to a detector block. An LUT corresponding to a detector block may be used to determine positions of crystals in the detector block corresponding to radiation events. As a still another example, if the feature information determined in 1006 includes time information relating to radiation events, the second set of data may include a count profile relating to coincidence events corresponding to multiple LORs. The count profile may include coincidence event counts corresponding to each of the multiple LORs in the detector and offsets of the multiple LORs in the detector.

In 1010, a correction profile relating to the detector may be determined based on the second set of data. Operation 1010 may be performed by the correction profile generation sub-unit 526. In some embodiments, the correction profile may include one or more correction file. A correction file may correspond to a feature parameter with respect to energy performance, time performance, position performance, or the like, or a combination thereof, as described elsewhere in the present disclosure. See, for example, FIG. 7 and description thereof. In some embodiments, a correction file corresponding to a feature parameter relating to the detector may include a plurality of correction coefficients. Each of the plurality of correction coefficients may correspond to a detector block in the detector. Each of the plurality of correction coefficients corresponding to a detector block may be used to correct feature information (e.g., energy value, positions, an offset of an LOR, etc.) relating to radiation events detected by the detector block.

In some embodiments, the plurality of correction coefficients may be determined based on the second set of data. For example, if the second set of data includes multiple groups of single events and energy values corresponding to each of the single events. A correction coefficient corresponding to the detector block may be determined based on an energy peak corresponding to the detector block. Furthermore, the correction coefficient corresponding to the detector block may be equal to a ratio of a target energy value to the energy peak corresponding to the detector block. In some embodiments, the target energy value may be set according to the energy of a radiation photon emitted from the subject. For example, the target energy value corresponding to a gamma photon may be set as 511 keV.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 1004 may be omitted. As another example, operations 1002 and 1004 may be performed simultaneously. In some embodiments, the feature information included in the first set of data may be extracted by, for example, the electronics module 116.

FIG. 11 is a flowchart illustrating an exemplary process 1100 for determining source data for determining a correction profile according to some embodiments of the present disclosure. In some embodiments, one or more operations of process 1100 illustrated in FIG. 11 may be implemented in the PET system 100 illustrated in FIG. 1. For example, the process 1100 illustrated in FIG. 11 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Operation 1002 as described in FIG. 10 may be performed according to process 1100.

In 1102, scanning data relating to the subject may be obtained. Operation 1104 may be performed by the data acquisition module 402. In some embodiments, the scanning data relating to the subject may include raw data (e.g., projection data) relating to the subject, personalized data relating to the subject, etc. The raw data (e.g., projection data) relating to the subject may relate to radiation events as described elsewhere in the present disclosure. See, for example, FIG. 10 and description thereof. The personalized data relating to the subject may include age, gender, height, weight, health history, occupation, etc.

In 1104, a determination may be made as to whether the subject satisfies a first condition. Operation 1104 may be performed by the data assessment sub-unit 522. If the subject satisfies the first condition, process 1100 may proceed to operation 1106. If the subject does not satisfy the first condition, process 1100 may proceed to operation 1102.

In some embodiments, the first condition may include a parameter relating to the subject. The parameter relating to the subject may represent a status of the subject. In some embodiments, the parameter relating to the subject may be estimated based on the personalized data relating to the subject. Exemplary parameters relating to the subject may include a weight, height, age, a body mass index (BMI), a respiration rate, a heart rate, a blood pressure, etc. In some embodiments, the first condition may include a first threshold corresponding to the parameter relating to the subject. If the parameter relating to the subject exceeds the first threshold, the subject may be considered satisfying the first condition. If the parameter relating to the subject is lower than or equal to the first threshold, the subject may be considered not satisfying the first condition. In some embodiments, the first condition may include a first range. If the parameter relating to the subject is within the first range, the subject may be considered satisfying the first condition. If the parameter relating to the subject is outside the first range, the subject may be considered not satisfying the first condition. The first threshold and for the first range may be set by a user via the terminal 140 or according to a default setting of the PET system 100.

In 1106, a determination may be made as to whether the raw data relating to the subject satisfies a second condition relating to a quality of the at least one portion of scanning data. Operation 1106 may be performed by the data assessment sub-unit 522. If the raw data relating to the subject satisfies the second condition, process 1100 may proceed to operation 1108. If the raw data relating to the subject does not satisfy the second condition, process 1100 may proceed to operation 1102.

The quality of the raw data may be represented by the number of true coincidence events (also referred to as a true coincidence event count) corresponding to the raw data. In some embodiments, the true coincidence event count may be evaluated based on a quality parameter. The quality parameter of the raw data may include and/or relate to a distribution of radiation events corresponding to LORs in the detector, a count of coincidence events, a noise equivalent counts ratio, a count of true coincidence events, a count of scatter coincidence events, a count of random coincidence events, etc. For example, the larger the half width of the distribution of radiation events corresponding to LORs in the detector is, the better the quality of the raw data may be. As another example, the greater the noise equivalent counts ratio relating to the raw data is, the better the quality of the raw data may be. The noise equivalent counts ratio may relate to, for example, a count of true coincidence events, a count of scatter coincidence events, a count of random coincidence events, etc. The greater the count of true coincidence events is, the smaller the count of scatter coincidence events and/or the count of random coincidence events are, the greater the noise equivalent counts ratio may be.

In some embodiments, the second condition may include a second threshold corresponding to the quality parameter relating to the raw data. In some embodiments, the second condition may be satisfied if the quality parameter (e.g., a count of scatter coincidence events and/or random coincidence events) relating to the raw data is lower than the second threshold. In some embodiments, the second condition may be satisfied if the quality parameter (e.g., a count of a true coincidence events, noise equivalent counts ratio, a half width of the distribution of radiation events corresponding to LORs, etc.) relating to the raw data exceeds the second threshold.

In some embodiments, the second condition may include a second range corresponding to the quality parameter relating to the raw data. If the quality parameter relating to the raw data is within the second range, the raw data may be considered satisfying the second condition. If the quality parameter relating to the raw data is outside the second range, the raw data may be considered not satisfying the second condition. The second threshold and/or the second range may be set by a user according to clinical demands (e.g., the type of a tissue or organ of interest) or according to a default setting of the PET system 100.

In 1108, a determination may be made as to whether the raw data relating to the subject satisfies a third condition relating to a quantity of the raw data. Operation 1108 may be performed by the data assessment sub-unit 522. If the raw data relating to the subject satisfies the third condition, process 1100 may proceed to operation 1110. If the raw data relating to the subject does not satisfy the second condition, process 1100 may proceed to operation 1102. In some embodiments, the quantity of the raw data may be estimated based on a count of the radiation events included in the raw data.

In some embodiments, the third condition may include a third threshold corresponding to the quantity of the raw data. As used herein, the quantity of the raw data may refer to the number of radiation events (also referred to as a radiation event count) corresponding to the raw data. The third condition may be satisfied if the quantity of the raw data exceeds the third threshold. The third condition may be not satisfied if the quantity raw data is lower than or equal to the third threshold. In some embodiments, the third condition may include a third range corresponding to the quantity of the raw data. The third condition may be satisfied if the quantity of the raw data within the third threshold. The third condition may be not satisfied if the quantity raw data is outside the third range. In some embodiments, the third threshold and/or the third range may be set by a user according to clinical demands (e.g., the type of a tissue being examined) or according to a default setting of the PET system 100.

In 1110, the raw data may be designated as source data for determining a correction profile, Operation 1110 may be the data assessment sub-unit 522.

Figure 12:
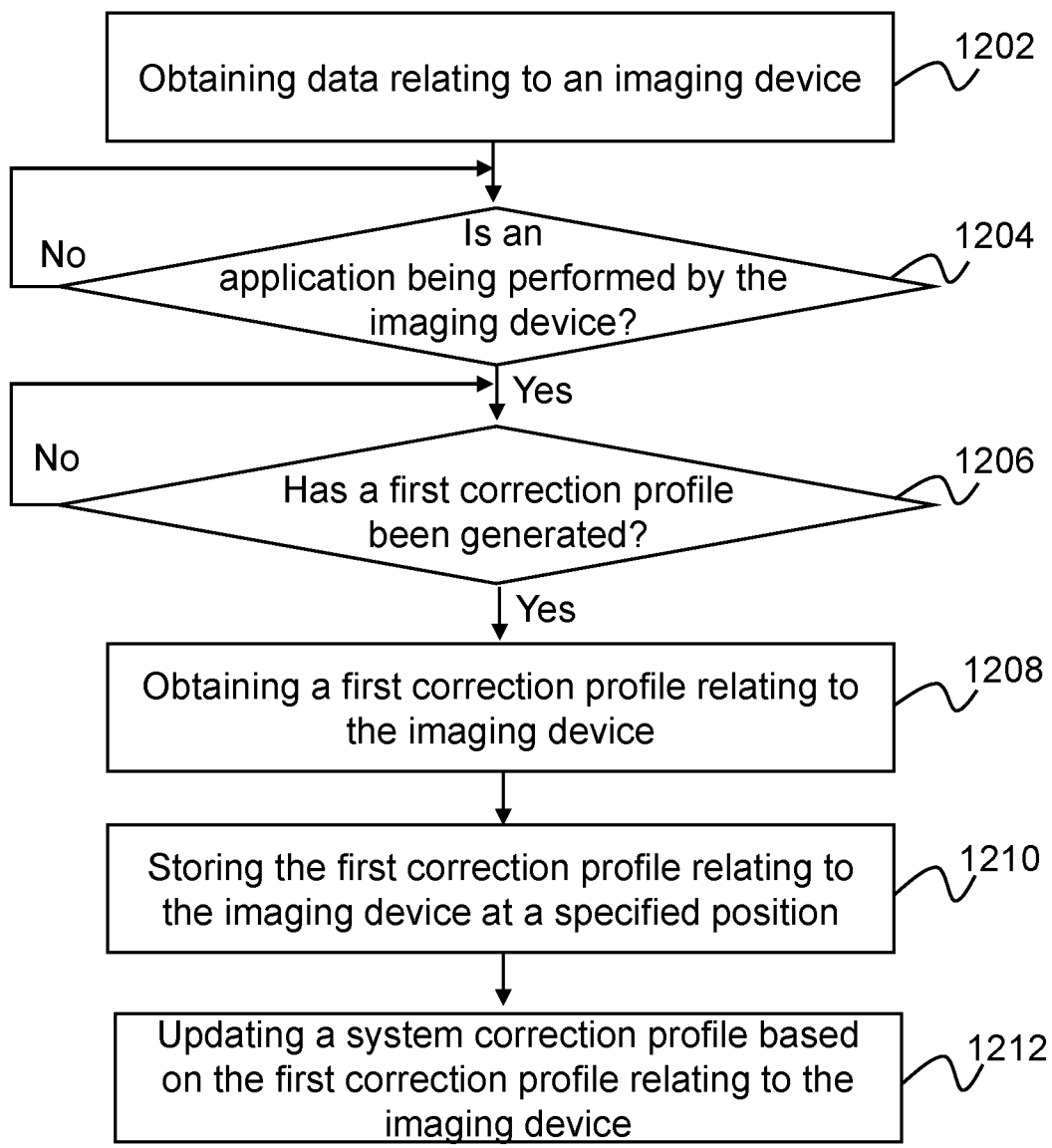
FIG. 12 is a flowchart illustrating an exemplary process for updating a system correction profile according to some embodiments of the present disclosure.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 1104 may be omitted. As another example, operations 1106 and 1108 may be performed simultaneously, FIG. 12 is a flowchart illustrating an exemplary process 1200 for updating a system correction profile according to some embodiments of the present disclosure. In some embodiments, one or more operations of process 1200 illustrated in FIG. 12 may be implemented in the PET system 100 illustrated in FIG. 1. For example, the process 1200 illustrated in FIG. 12 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Operation 708 as described in FIG. 12 may be performed according to process 1200.

In 1202, the data relating to an imaging device may be obtained. Operation 1202 may be performed by the correction profile updating unit 530. The imaging device may include a medical imaging device (e.g., the scanner 110) as described elsewhere in the present disclosure. See, for example, FIG. 1 and description thereof. In some embodiments, the data relating to the imaging device may include a determination relating to perform a correction relating to the imaging device. In some embodiments, the determination relating to perform a correction relating to the imaging device may be obtained from the detector assessment unit 510. In some embodiments, the determination relating to perform a correction relating to the imaging device may be obtained from the terminal 140 made by, for example, a user.

In 1204, a determination may be made as to whether an application is being performed by the imaging device. Operation 1204 may be performed by the correction profile updating unit 530. If the application is being performed, process 1200 may proceed to 1206. If the application is not being performed, operation 1204 may be repeated until it is determined that an application is being performed. The application relating to the imaging device may include a clinical examination application, a service examination application, or the like, or a combination thereof. As used herein, the clinical examination application may refer to a scan relating to a subject performed by the imaging device. The service examination application may include that that a subject to be examined is being scanned by the imaging device.

In 1206, a determination may be made as to whether a correction profile has been generated. Operation 1206 may be performed by the correction profile updating unit 530. If the correction profile has been generated, process 1200 may proceed to 1208. If the correction profile has been not generated, operation 1206 may be repeated until it is determined that the correction profile has been generated.

In some embodiments, the correction profile updating unit 530 may determine whether the correction profile has been generated based on an instruction inputted by a user via the terminal 140. In some embodiments, the correction profile updating unit 530 may determine whether the correction profile has been generated based on an instruction transferred from the correction profile determination unit 520. For example, if the correction profile has been generated by the correction profile determination unit 520, the correction profile determination unit 520 may generate an instruction relating to a generation of the correction profile and transfer the instruction relating to the generation of the correction profile to the correction profile updating unit 530. Then, the correction profile updating unit 530 may determine that the correction profile has been generated.

In 1208, a correction profile relating to the imaging device may be obtained. Operation 1208 may be performed by the acquisition module 402. In some embodiments, the correction profile may be obtained from the storage 130, the storage 220, the memory 360, the storage 390, the correction profile determination unit 520, the storage unit 560, and/or other storages.

In 1210, the correction profile relating to the imaging device may be stored at a specified position. Operation 1210 may be performed by the correction profile updating unit 530. In some embodiments, the specified position may correspond to a running directory relating to the correction profile. The correction profile relating to the imaging device may be stored in the running directory. In some embodiments, the running directory may be set by a user via the terminal 140 or according to a default setting of the PET system 100. For example, the running directory of the correction profile may be stored in the storage 130, the storage 220, the memory 360, the storage 390, the correction profile determination unit 520, the storage unit 560, and/or other storages.

In 1212, a system correction profile may be updated based on the correction profile relating to the imaging device. Operation 1212 may be performed by the correction profile updating unit 530. In some embodiments, the system correction profile may include multiple correction profiles. At least one of the multiple correction profiles in the system correction profile may be replaced by the correction profile. In some embodiments, the system correction profile may include a plurality of first correction coefficients. The correction profile may include a plurality of second correction coefficients. At least one portion of the plurality of first correction coefficients may be replaced by at least one portion of the plurality of second correction coefficients corresponding to the at least one portion of the plurality of first correction coefficients.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or both of operations 1202 and 1210 may be omitted. As another example, operations 1206 and 1208 may be performed simultaneously.

Figure 13:
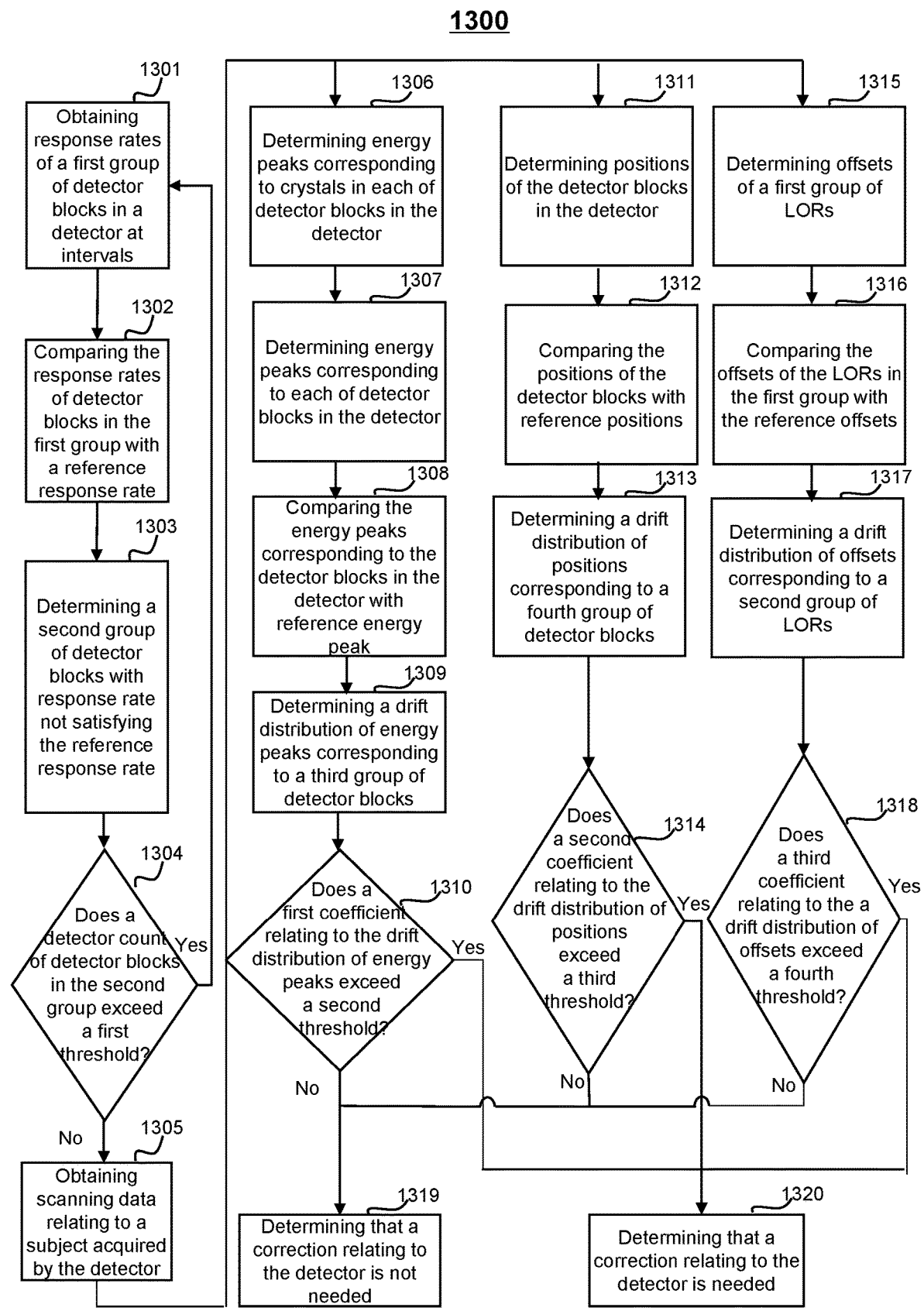
FIG. 13 is a flowchart illustrating an exemplary process for determining whether to perform a correction relating to a detector according to some embodiments of the present disclosure.

FIG. 13 is a flowchart illustrating an exemplary process 1300 for determining whether to perform a correction relating to a detector according to some embodiments of the present disclosure. In some embodiments, one or more operations of process 1300 illustrated in FIG. 13 may be implemented in the PET system 100 illustrated in FIG. 1. For example, the process 1300 illustrated in FIG. 13 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Process 800 as described in FIG. 8 may be performed according to process 1300.

In 1301, response rates of a first group of detector blocks in a detector of an imaging device may be obtained. Operation 1301 may be performed by the acquisition module 402. The response rates of the first group of detector blocks may be obtained from the scanner 110, the storage 130, the terminal 140, and/or any other storage. For example, the response rates of the first group of detector blocks may be obtained from the scanner 110 determined by the electronics module 116 in the detector 114. A detector block count of detector blocks belonging to the first group may be lower than or equal to the total detector block count of detector blocks in the detector. The detector block count of detector blocks belonging to the first group may be set by a user via the terminal 140 or according to a default setting of the PET system 100. A detector block in the first group may be selected from the total detector blocks in the detector manually or automatically.

In 1302, the response rates of the first group of detector blocks may be compared with a reference response rate. Operation 1302 may be performed by the comparison sub-unit 514. In some embodiments, the reference response rate may be set by a user via the terminal 140 or according to a default setting of the PET system 100. In some embodiments, the reference response rate may correspond to a factory setting of the imaging device.

In 1303, a second group of detector blocks with response rate not satisfying the reference response rate may be determined. Operation 1303 may be performed by the comparison sub-unit 514. A response rate of a detector block in the second group not satisfying the reference response rate may include a difference between the response rate of the detector block and the reference response rate may exceed a reference value. The reference value may be set by a user via the terminal 140 or according to a default setting of the PET system 100.

In 1304, a determination may be made as to whether a detector block count of detector blocks in the second group exceeds a first threshold. Operation 1304 may be performed by the judgment sub-unit 516. If the detector block count of detector blocks in the second group exceeds the first threshold, process 1300 may proceed to operation 1305. If the detector block count of detector blocks in the second group is lower than or equal to the first threshold, process 1300 may proceed to operation 1301, The first threshold may be set by a user via the terminal 140 or according to a default setting of the PET system 100.

In 1305, scanning data relating to a subject acquired by the detector may be obtained. Operation 1305 may be performed by the acquisition module 402. The scanning data relating to the subject may include feature information relating to radiation events as described elsewhere in the present disclosure. See, for example, FIG. 8 and FIG. 9 and descriptions thereof. The detector may include multiple detector blocks. Each of the multiple detector blocks may include at least one crystal as described in connection with FIG. 1.

In 1306, energy peaks corresponding to crystals in each of detector blocks in the detector may be determined. Operation 1306 may be performed by the first feature determination sub-unit 512. A crystal in a detector block may detect multiple radiation events. An energy value may correspond to a certain radiation event count of radiation events. An energy peak corresponding to the crystal may refer to an energy value corresponding to a maximum radiation event count of radiation events.

In 1307, energy peaks corresponding to each of detector blocks in the detector may be determined. Operation 1307 may be performed by the first feature determination sub-unit 512. An energy peak corresponding to a detector block may refer to an energy value corresponding to a maximum radiation event count of radiation events. An energy peak corresponding to a detector block may be determined based on energy peaks corresponding to crystals in the detector block. An energy peak corresponding to one of the crystals in the detector block having a maximum radiation event count of radiation events may be designated as the energy peak corresponding to the detector block.

In 1308, the energy peaks corresponding to the detector blocks in the detector may be compared with a reference energy peak. Operation 1308 may be performed by the comparison sub-unit 514. In some embodiments, the reference energy peak may be set by a user via the terminal 140 or according to a default setting of the PET system 100. Furthermore, the reference energy peak may be set based on a most recent correction relating to the detector.

In 1309, a drift distribution of energy peaks corresponding to a third group of detector blocks may be determined. Operation 1309 may be performed by the comparison sub-unit 514. A detector block in the third group may have an energy peak not satisfying the reference energy peak. For example, if a difference between an energy peak corresponding to a detector block in the third group and the reference energy peak is outside a first range, the energy peak corresponding to the detector block may not satisfy the reference energy peak. The first range may be set by a user via the terminal 140 or according to a default setting of the PET system 100. The drift distribution of energy peaks may indicate a relationship of a difference between an energy peak corresponding to a detector block in the third group and the reference energy peak and a detector block count of detector blocks in the third group corresponding to the difference.

In 1310, a determination may be made as to whether a first feature parameter relating to the drift distribution of energy peaks exceeds a second threshold, Operation 1310 may be performed by the judgment sub-unit 516, If the first feature parameter exceeds the second threshold, process 1300 may proceed to operation 1320. If the first feature parameter is lower than or equal to the second threshold, process 1300 may proceed to operation 1319. The second threshold may be set by a user via the terminal 140 or according to a default setting of the PET system 100, The first parameter relating to the drift distribution of energy peaks may be determined based on the drift distribution of energy peaks. For example, the first feature parameter may include a mean value of the drift distribution of energy peaks, a standard deviation of the drift distribution of energy peaks, an integral value of the drift distribution of energy peaks within an interval, etc.

In 1311, positions of the first group of detector blocks may be determined. Operation 1311 may be performed by the first feature determination sub-unit 512, A position of a detector block in the detector may be determined based on positions of crystals in the detector block. Positions of crystals in a detector block may be represented by a position spectrum determined based on position information included in the scanning data obtained in 1305. In some embodiments, a position of a detector block may correspond to a center position of a position spectrum of crystals in the detector block.

In 1312, the positions of the detector blocks in the detector may be compared with reference positions. Operation 1312 may be performed by the comparison sub-unit 514. In some embodiments, the reference positions may be set by a user via the terminal 140 or according to a default setting of the PET system 100. Furthermore, the reference positions may be set corresponding to a most recent correction relating to the detector.

In 1313, a drift distribution of positions corresponding to a fourth group of detector blocks may be determined. Operation 1313 may be performed by the comparison sub-unit 514. A detector block in the fourth group may have a position not satisfying a reference position corresponding to the detector block. For example, if a difference between a position corresponding to a detector block in the third group and a reference position corresponding to the detector block is outside a second range, the position of the detector block may be considered not satisfying the reference position corresponding to the detector block. The third range may be set by a user via the terminal 140 or according to a default setting of the PET system 100. The drift distribution of positions may indicate a relationship of a difference between a position corresponding to a detector in the fourth group and the reference position corresponding to the detector in the fourth group and a detector block count corresponding to the difference.

In 1314, a determination may be made as to whether a second feature parameter relating to the drift distribution of positions exceeds a third threshold. Operation 1314 may be may be performed by the judgment sub-unit 516. If the second feature parameter exceeds the third threshold, process 1300 may proceed to operation 1320. If the second feature parameter is lower than or equal to the third threshold, process 1300 may proceed to operation 1319. The third threshold may be set by a user via the terminal 140 or according to a default setting of the PET system 100. The second feature parameter relating to the drift distribution of positions may be determined based on the drift distribution of positions. For example, the second feature parameter may include a mean value of the drift distribution of positions, a standard deviation of the drift distribution of positions, an integral value of the drift distribution of positions within an interval, etc.

In 1315, offsets of a first group of LORs may be determined. Operation 1315 may be performed by the first feature determination sub-unit 512. The offsets of the first group of LORs may be determined based on time information included in the scanning data obtained in 1305.

In 1316, the offsets of the first group of LORs may be compared with reference offsets. Operation 1316 may be performed by the comparison sub-unit 514. In some embodiments, the reference offsets may be set by a user via the terminal 140 or according to a default setting of the PET system 100. For example, the reference offsets may be set corresponding to a most recent correction relating to the detector.

In 1317, a drift distribution of offsets corresponding to a second group of LORs may be determined. Operation 1317 may be performed by the comparison sub-unit 514. An LOR in the second group may have an offset not satisfying a reference offset corresponding to the LOR. For example, if a difference between an offset corresponding to an LOR and a reference offset corresponding to the LOR is outside a third range, the offset of the LOR may be considered not satisfying the reference offset corresponding to the LOR. The fourth range may be set by a user via the terminal 140 or according to a default setting of the PET system 100. The drift distribution of offsets may indicate a relationship of a difference between an offset of an LOR in the second group and a reference offset corresponding to the LOR and an LOR count corresponding to the difference.

In 1318, a determination may be made as to whether a third parameter relating to the drift distribution of offsets exceeds a fourth threshold. Operation 1318 may be may be performed by the judgment sub-unit 516. If the third parameter exceeds the fourth threshold, process 1300 may proceed to operation 1320. If the third parameter is lower than or equal to the fourth threshold, process 1300 may proceed to operation 1319. The fourth threshold may be set by a user via the terminal 140 or according to a default setting of the PET system 100. The third parameter relating to the drift distribution of offsets may be determined based on the drift distribution of offsets. For example, the third parameter may include a mean value of the drift distribution of offsets, a standard deviation of the drift distribution of offsets, an integral value of the drift distribution of offsets within an interval, etc.

In 1319, a determination may be made as to that a correction relating to the detector is not needed. Operation 1319 may be may be performed by the judgment sub-unit 516.

In 1320, a determination may be made as to that a correction relating to the detector is needed. Operation 1320 may be may be performed by the judgment sub-unit 516.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 1306-1310, one or more of operations 1311-1314, and/or operations 1315-1318 may be omitted. As another example, operations 1301-1305 may be omitted.

Figure 14:
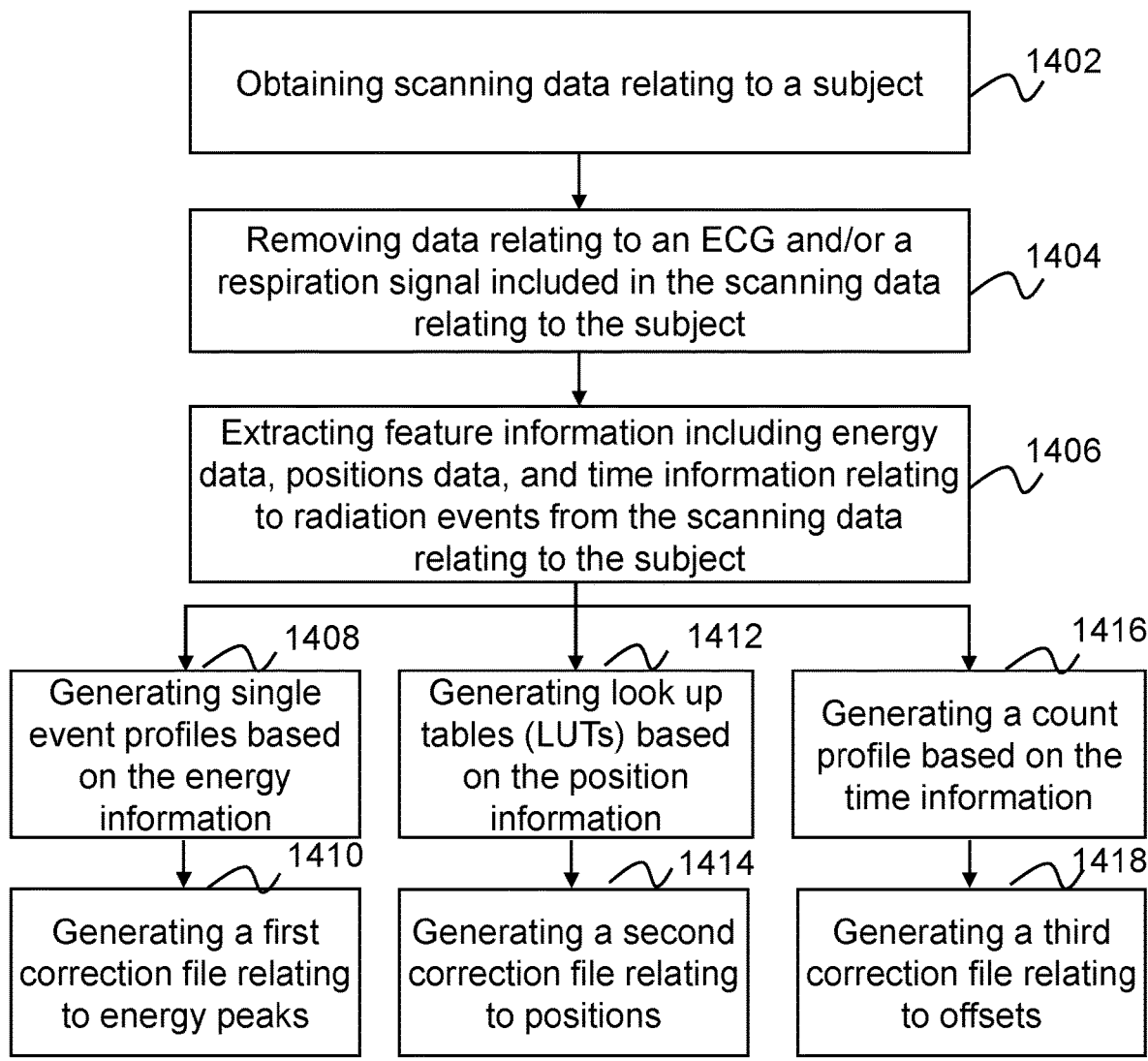
FIG. 14 is a flowchart illustrating an exemplary process for determining a correction profile relating to a detector according to some embodiments of the present disclosure.

FIG. 14 is a flowchart illustrating an exemplary process 1400 for determining a correction relating to a detector according to some embodiments of the present disclosure. In some embodiments, one or more operations of process 1400 illustrated in FIG. 14 may be implemented in the PET system 100 illustrated in FIG. 1. For example, the process 1400 illustrated in FIG. 14 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Process 1000 as described in FIG. 10 may be performed according to process 1400.

Figure 15:
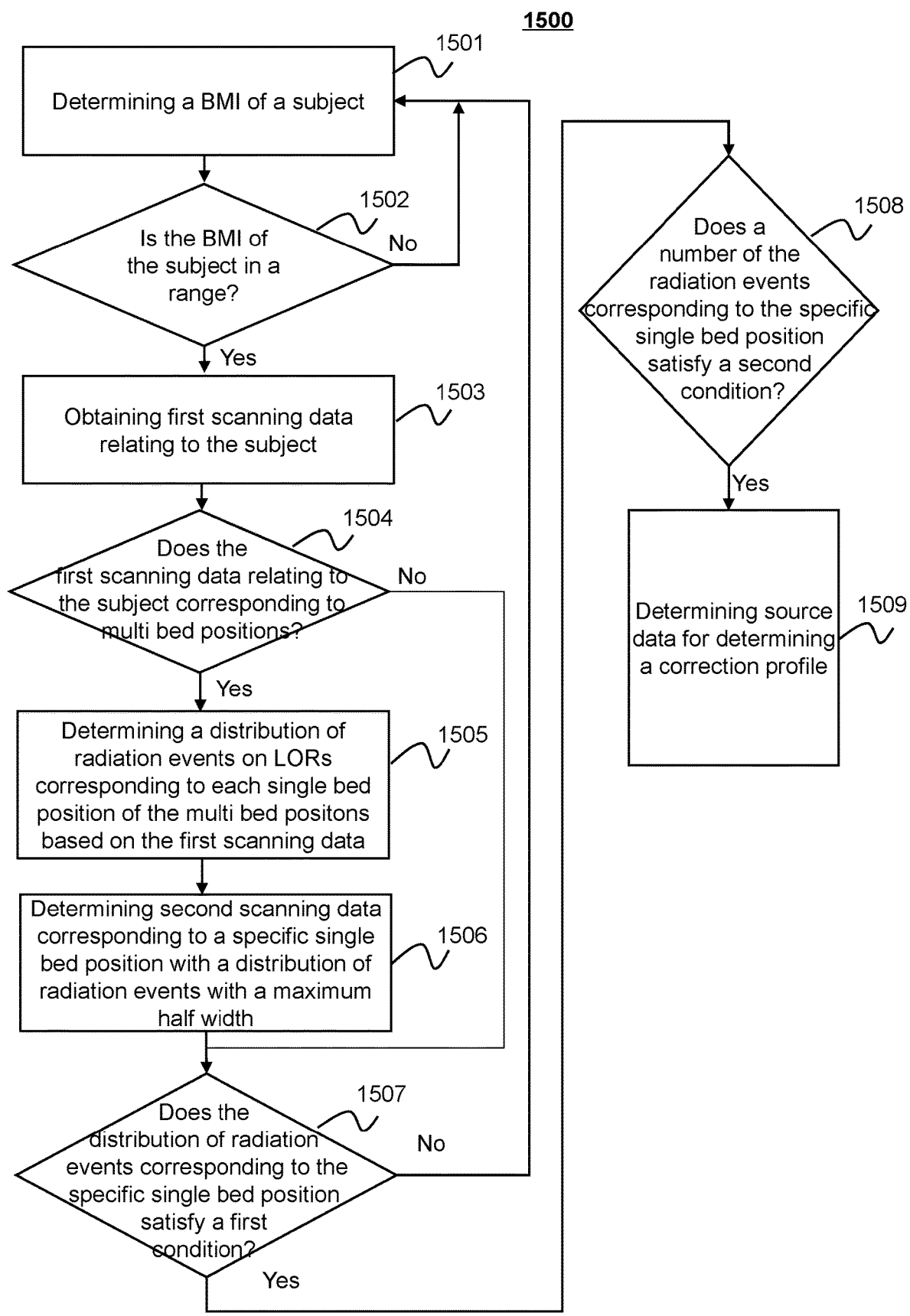
FIG. 15 is a flowchart illustrating an exemplary process for determining source data for determining a correction profile relating to a detector according to some embodiments of the present disclosure.

In 1402, scanning data relating to a subject may be obtained. Operation 1402 may be performed by the data assessment sub-unit 522. The scanning data relating to the subject may be determined according to process 1500 as illustrated in FIG. 15. The scanning data relating to the subject may be acquired by a detector in an imaging device corresponding to detected radiation photons emitted from the subject.

In 1404, data relating to an ECG and/or a respiration signal may be removed from the scanning data relating to the subject. Operation 1404 may be performed by the data assessment sub-unit 522. In some embodiments, the scanning data relating to the subject may be acquired by the imaging device based on a physiological signal, for example, an ECG signal, a respiration signal, etc. For example, if the scanning data is acquired by the imaging device (e.g., the scanner 110) based on a foresight ECG gating technique, the scanning data may include multiple ECG signals. The multiple ECG signals may be separated from the scanning data. As another example, if the scanning data is acquired by the imaging device (e.g., the scanner 110) based on a retrospective ECG gating technique, the scanning data may include at least one portion of data relating to movements of the subject. The at least one portion of data relating to the movements of the subject may be removed from the scanning data based on an ECG signal collected simultaneously from the subject.

In 1406, feature information may be extracted from the scanning data relating to the subject. Operation 1406 may be performed by the second feature determination sub-unit 524. The feature information may include energy information, position information, and/or time information as described elsewhere in the disclosure. See, for example, FIG. 7 and the disclosure thereof. The feature information may be extracted from the scanning data (e.g., scintillation pulses) based on a feature extraction technique corresponding to the energy information, the position information, and the time information, respectively. More descriptions for the feature extraction technique may be found elsewhere in the present disclosure. See, for example, FIG. 10 and the disclosure thereof.

In 1408, multiple single event profiles may be generated based on the energy information. Operation 1408 may be performed by the second feature determination sub-unit 524. Each of the multiple single event profiles may correspond to a detector block in the detector. A single event profile may include multiple groups of single events, an energy value corresponding to each group of the multiple groups of single events, and a single event count of single events in each group of the multiple groups of single events. Single events in each group of the multiple groups of single events may correspond to the same energy value.

In 1410, a first correction file relating to an energy value of single event may be generated based on the single event profile. Operation 1410 may be performed by the correction profile generation sub-unit 526. The first correction file relating to the energy value of single event may include a plurality of first correction coefficients. Each of the plurality of first correction coefficients may correspond to a detector block. A first correction coefficient corresponding to a detector block may be determined based on an energy peak of an energy distribution corresponding to the detector block and a target energy peak. The energy distribution corresponding to the detector block may be determined based on the single event profile corresponding to the detector block. Furthermore, a first correction coefficient in the first correction file may be equal to a ratio of the target energy peak to an energy peak corresponding to each of the detector blocks in the detector.

In 1412, multiple look up tables (LUTs) may be generated based on the position information. Operation 1412 may be performed by the second feature determination sub-unit 524. Each of the multiple groups of look up tables (LUTs) may correspond to a detector block in the detector. An LUT corresponding to a detector block may be used to determine positions of crystals in the detector block corresponding to radiation events. An LUT may include a position spectrum corresponding to each of the detector blocks in the detector and a position distribution of single events corresponding to the position spectrum.

In 1414, a second correction file relating to positions may be generated. Operation 1414 may be performed by the correction profile generation sub-unit 526. In some embodiments, if a position distribution of single events corresponding to a position spectrum in an LUT satisfies a reference position distribution of single events, the second correction file may include the multiple position spectrums corresponding to each of the detector blocks in the detector. If a position distribution of single events corresponding to each of the detector blocks does not satisfy a target position distribution of single events, the second correction file may be determined based on position distributions of single events corresponding to each of the detector blocks and the target position distributions.

In 1416, a count profile may be generated based on the time information. Operation 1416 may be performed by the second feature determination sub-unit 524. The count profile may include multiple coincidence event distributions corresponding to each of LORs in the detector. A coincidence event distribution may indicate a relationship between an offset of an LOR and a coincidence event count corresponding to the offset of the LOR.

In 1418, a third correction file relating to offsets may be generated. Operation 1418 may be performed by the correction profile determination sub-unit. The third correction file relating to offsets may include a plurality of third correction coefficients. Each of the plurality of third correction coefficients may correspond to an LOR. A third correction coefficient corresponding to an LOR may be determined based on a coincidence event distribution corresponding to an LOR. Furthermore, a third correction coefficient in the third correction file may be equal to a ratio of a target offset to an offset peak having a maximum coincidence event count in a coincidence event distribution.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 1412 and 1414, and/or operations 1416 and 1418 may be omitted. As another example, operation 1404 may be omitted.

FIG. 15 is a flowchart illustrating an exemplary process 1500 for determining source data for determining a correction profile relating to a detector according to some embodiments of the present disclosure. In some embodiments, one or more operations of process 1500 illustrated in FIG. 15 may be implemented in the PET system 100 illustrated in FIG. 1. For example, the process 1500 illustrated in FIG. 15 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Process 1100 as described in FIG. 11 may be performed according to process 1500.

In 1501, a BMI of a subject may be determined. Operation 1501 may be performed by the comparison sub-unit 514. The BMI of the subject may be determined based on the height and weight of the subject.

In 1502, a determination may be made as to whether the BMI of the subject may be in a range. Operation 1502 may be performed by the judgment sub-unit 516. If the BMI of the subject is in the range, process 1500 may proceed to 1503. If the BMI of the subject may is outside the range, process 1500 may proceed to 1501.

In 1503, the first scanning data relating to the subject may be obtained. Operation 1503 may be performed by the acquisition module 402. The first scanning data relating to the subject may correspond to multi bed positions or single bed position. As used herein, the single bed position may mean that the subject and the detector are relatively stationary during a scanning procedure. The multi bed positions may mean that the subject may move to multiple positions relative to the detector in a scanning procedure.

In 1504, a determination may be made as to whether the first scanning data relating to the subject corresponds to multi bed positions. Operation 1504 may be performed by the judgment sub-unit. If the first scanning data relating to the subject corresponds to the multi bed positions, process 1500 may proceed to 1505. If the first scanning data relating to the subject corresponds to the single bed position, process 1500 may proceed to 1507.

In 1505, a distribution of radiation events on LORs corresponding to each single bed position of the multi bed positions may be determined based on the first scanning data. Operation 1505 may be performed by the comparison sub-unit 514. The radiation events may include multiple coincidence events. A distribution of radiation events on the LORs corresponding to a single bed position may indicate a coincidence event count corresponding to each of the LORs.

In 1506, second scanning data corresponding to a specific single bed position may be determined. Operation 1506 may be performed by the comparison sub-unit 514. The second scanning data corresponding to the specific single bed may correspond to a distribution of radiation events on the LORs having a maximum half width.

In 1507, a determination may be made as to whether the distribution of radiation events corresponding to the specific single bed position satisfies a first condition. Operation 1507 may be performed by the judgment sub-unit 516. If the first distribution of radiation events satisfies the first condition, process 1500 may proceed to 1508. If the first distribution of radiation events does not satisfy the first condition, process 1500 may proceed to 1501. In some embodiments, the distribution of the radiation events may be determined based on the second scanning data determined in 1506 if the first scanning data corresponds to the multi bed position. In some embodiments, the distribution of the radiation events may be determined based on the first scanning data obtained in 1503 if the first scanning data corresponds to a single bed position. The first condition may relate to a parameter of the distribution of radiation events, for example, a half width of the distribution of radiation events, a mean value of the distribution of radiation events, a standard deviation of the distribution of radiation events, etc. In some embodiments, the first condition may include a first threshold corresponding to the parameter of the distribution of radiation events. If the parameter of the distribution of radiation events exceeds the first threshold, the distribution of radiation events corresponding to the single bed position may be considered satisfying the first condition. If the parameter of the distribution of radiation events is equal to or less than the first threshold, the distribution of radiation events corresponding to the single bed position may be considered does not satisfying the first condition.

In 1508, a determination may be made as to whether the number of the radiation events (or referred to as a radiation event count) corresponding to the specific single bed position satisfies a second condition. Operation 1508 may be performed by the judgment sub-unit 516. If the radiation event count corresponding to the specific single bed position satisfies the second condition, process 1500 may proceed to 1509. In some embodiments, the second condition may include a second threshold. If the radiation event count corresponding to the specific single bed position exceeds the second threshold, the quantity of the radiation events corresponding to the single bed position may be considered satisfying the second condition.

In 1509, source data for determining a correction profile ray be determined. Operation 1509 may be performed by the judgment sub-unit 516. In some embodiments, the source data for determining the correction profile may include the first scanning data acquired in operation 1503 if the first scanning data corresponds to single bed position. In some embodiments, the source data for determining the correction profile may include the second scanning data determined in operation 1506 if the first scanning data corresponds to multi bed positions.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operations 1501 and 1502 may be unnecessary.

Figure 16:
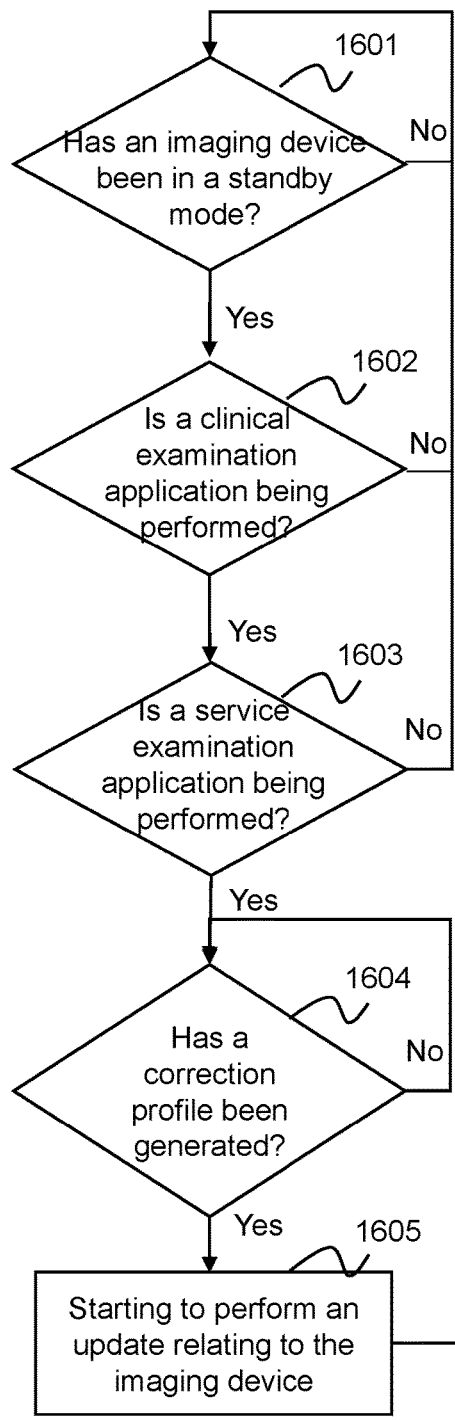
FIG. 16 is a flowchart illustrating an exemplary process for updating a correction profile relating to a detector in an imaging system according to some embodiments of the present disclosure.
Figure 16:
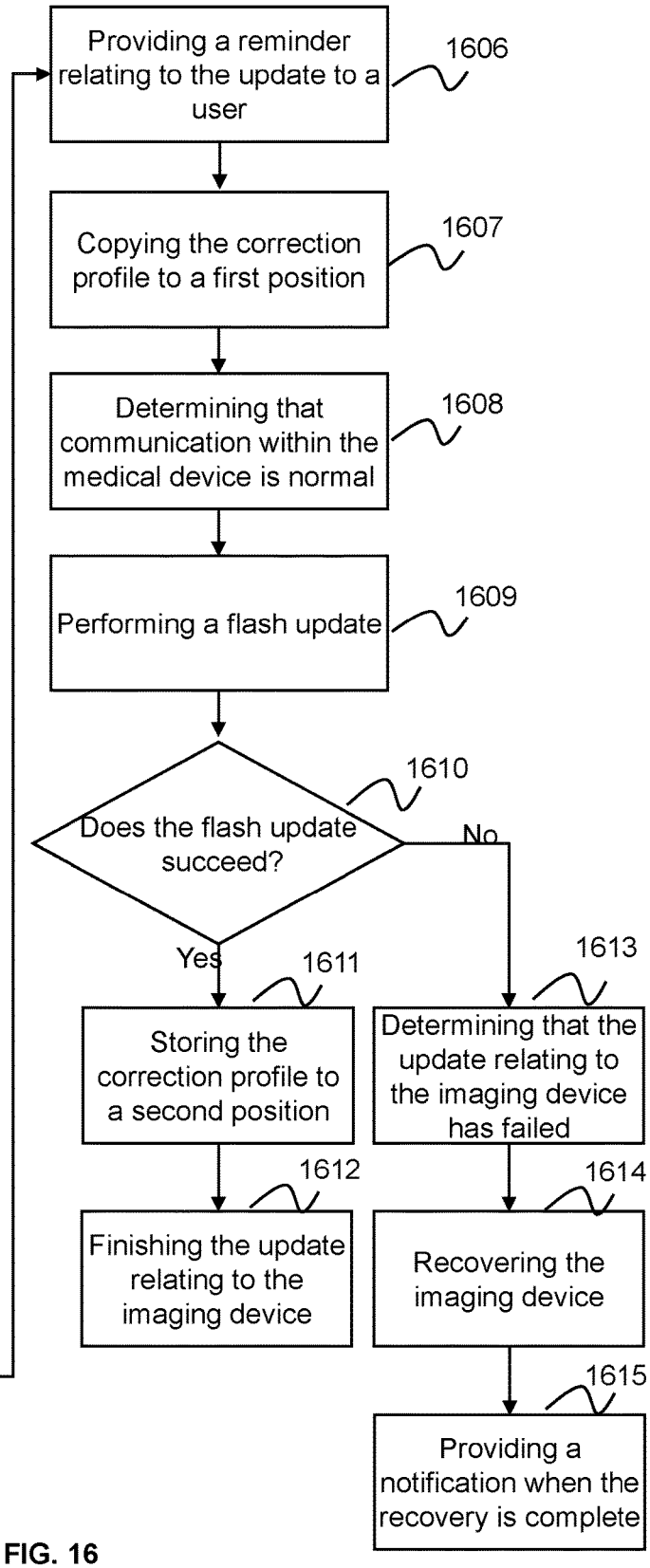

FIG. 16 is a flowchart illustrating an exemplary process 1600 for updating a correction profile relating to a detector according to some embodiments of the present disclosure. In some embodiments, one or more operations of process 1600 illustrated in FIG. 16 may be implemented in the PET system 100 illustrated in FIG. 1. For example, the process 1600 illustrated in FIG. 16 may be stored in the storage 130 in the form of instructions, and invoked and/or executed by the processing device 120 (e.g., the processor 210 of the computing device 200 as illustrated in FIG. 2, the CPU 340 of the mobile device 300 as illustrated in FIG. 3). Process 1200 as described in FIG. 12 may be performed according to process 1600.

In 1601, a determination may be made as to whether an imaging device has been in a standby mode. Operation 1602 may be performed by the correction profile updating unit 530. If the imaging device has been in the standby mode, process 1600 may proceed to operation 1602. If the imaging device has been not in the standby mode, operation 1602 may be repeated until the imaging device is determined to be in the standby mode.

In 1602, a determination may be made as to whether a clinical examination application is being performed. Operation 1602 may be performed by the correction profile updating unit 530. If the clinical examination application is being performed, process 1600 may proceed to operation 1603. If the clinical examination application is not being performed, process 1600 may proceed to operation 1601.

In 1603, a determination may be made as to whether a service examination application is being performed. Operation 1603 may be performed by the correction profile updating unit 530. If the service examination application is being performed, process 1600 may proceed to operation 1604. If the service examination application is not being performed, process 1600 may proceed to operation 1601.

In 1604, a determination may be made as to whether a correction profile has been generated. Operation 1604 may be performed by the correction profile updating unit 530. If the correction profile has been generated, process 1600 may proceed to operation 1605. If the correction profile has not been generated, process 1600 may perform operation 1605 repeatedly until the correction profile has been generated.

In 1605, an update relating to the imaging device may be started to perform. Operation 1605 may be performed by the correction profile updating unit 530.

In 1606, a reminder relating to the update may be provided to a user. Operation 1606 may be performed by the correction profile updating unit 530. The reminder may be in, for example, text, voice, etc. In some embodiments, the reminder may be transferred to the terminal 140 for displaying to the user.

In 1607, the correction profile may be copied to a first position. Operation 1607 may be performed by the correction profile updating unit 530. In some embodiments, the first position may correspond to a present working directory relating to the update of the system correction profile. In some embodiments, the present working directory may be set by a user via the terminal 140 or according to a default setting of the PET system 100. Furthermore, the present working directory may set in the storage 220, the storage module 408, or the storage unit 550.

In 1608, a determination may be made as to that communication within the imaging device is normal. Operation 1608 may be performed by the correction profile updating unit 530.

In 1609, a flash update may be performed. Operation 1609 may be performed by the correction profile updating unit 530.

In 1610, a determination may be made as to whether the flash update succeed. Operation 1610 may be performed by the correction profile updating unit 530. If the flash update succeeds, process 1600 may proceed to operation 1611. If the flash update does not succeed, process 1600 may proceed to operation 1613.

In 1611, the correction profile may be stored to a second position. Operation 1611 may be performed by the correction profile updating unit 530. The second position may correspond to a running directory relating to the performing of the correction profile. In some embodiments, the running directory may be set by a user via the terminal 140 or according to a default setting of the PET system 100. Furthermore, the running directory may include the storage 130, the storage 220, the memory 360, the storage module 408, the storage unit 560, and/or other storages.

In 1612, the update relating to the imaging device may be finished. Operation 1605 may be performed by the correction profile updating unit 530.

In 1613, a determination may be made as to that the update relating to the imaging device has failed. Operation 1613 may be performed by the correction profile updating unit 530.

In 1614, the imaging device may be recovered. Operation 1614 may be performed by the correction profile updating unit 530.

In 1615, a notification may be provided when the recovery is complete. Operation 1615 may be performed by the correction profile updating unit 530. The notification may be in, for example, text, voice, etc. In some embodiments, the notification may be transferred to the terminal 140 for displaying to a user.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, one or more of operations 1601, 1602, and 1603 may be omitted.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on a computing device having at least one processor, at least one computer-readable storage medium, and a communication port connected to an imaging device including a detector, the detector including detector blocks, the method comprising:
   acquiring first scanning data relating to a subject, the first scanning data including personalized data relating to the subject and raw data relating to radiation events occurred in a positron emission tomography (PET) scan of the subject;
   determining whether the raw data satisfies a first condition by determining whether a count of the radiation events equals or exceeds a first threshold;
   determining whether the personalized data relating to the subject satisfies a second condition;
   in response to determining that the raw data satisfies the first condition and the personalized data satisfies the second condition, determining, based on the first scanning data, a correction profile relating to the imaging device; and
   calibrating, based on the correction profile, the imaging device.

2. The method of claim 1, wherein the personalized data includes a body mass index of the subject, and the determining whether the personalized data relating to the subject satisfies the second condition includes:
   determining whether the body mass index of the subject is in a range from a second threshold to a third threshold.

3. The method of claim 1, wherein the raw data relates to a distribution of the radiation events corresponding to lines of response, and the determining whether the raw data satisfies the first condition includes:
   determining whether a half width of the distribution of the radiation events corresponding to the lines of response equals or exceeds a fourth threshold.

4. The method of claim 1, wherein the method further includes:
   determining whether the first scanning data corresponds to multi bed positions or a single bed position, and the determining whether the raw data satisfies the first condition includes:
   in response to determining that the first scanning data corresponds to the single bed position, determining whether the raw data satisfies the first condition.

5. The method of claim 1, wherein the method further includes:
   determining whether the first scanning data corresponds to multi bed positions or a single bed position, and the determining whether the raw data satisfies the first condition includes:
   in response to determining that the first scanning data corresponds to the multi bed positions,
      determining a distribution of radiation events on lines of response corresponding to each single bed position of the multi bed positions based on the first scanning data;
      determining second scanning data corresponding to a specific single bed position of the multi bed positions based on the distribution of radiation events;
      determining whether the raw data satisfies the first condition by determining whether the second scanning data satisfies the first condition.

6. The method of claim 5, wherein the first scanning data includes a first sub-set of data and a second sub-set of data, the first sub-set of data being used in determining the correction profile relating to the imaging device, the second sub-set of data being determined by excluding the first sub-set of data from the second scanning data, and the preprocessing second scanning data to obtain the first scanning data includes:
   preprocessing second scanning data by removing, from the first scanning data, the second sub-set of data.

7. The method of claim 1, wherein the determining, based on the first scanning data, the correction profile further comprises:
   extracting feature information from the first scanning data;
   determining, based on the feature information, second scanning data relating to radiation events; and
   determining, based on the second scanning data, the correction profile relating to the imaging device, wherein the correction profile includes a plurality of correction coefficients corresponding to the feature information.

8. The method of claim 7, wherein the feature information relates to at least one of energy information of one of the radiation events, position information of the radiation events corresponding to the detector, or time information relating to detector blocks corresponding to a line of response.

9. The method of claim 8, wherein the second scanning data includes multiple groups of single events and energy values corresponding to each of the single events, each group of single events corresponding to a detector block that has detected the group of single events, and the correction profile includes a first correction file relating to energy peaks corresponding to the detector blocks, the first correction file including correction coefficients each of which corresponds to one of the detector blocks and is equal to a ratio of a target energy value to the energy peak corresponding to the detector block.

10. The method of claim 8, wherein the second scanning data includes multiple look up tables (LUTs) each of which includes a position spectrum corresponding to one of the detector blocks and a position distribution of single events corresponding to the position spectrum, and the correction profile includes a second correction file determined based on position distributions of single events corresponding to each of the detector blocks and target position distributions.

11. The method of claim 8, wherein the second scanning data includes a count profile including multiple coincidence event distributions corresponding to each of lines of response (LORs) in the detector, the correction profile includes a third correction file including correction coefficients each of which corresponds to an LOR, and each correction coefficient in the third correction file is determined based on a coincidence event distribution corresponding to an LOR.

12. The method of claim 1, wherein the in response to determining that the raw data satisfies the first condition and the personalized data satisfies the second condition, determining, based on the first scanning data, a correction profile relating to the imaging device further includes:
  determining whether the raw data satisfies a third condition based on a true coincidence event count corresponding to the radiation events; and
  in response to determining that the raw data satisfies the first condition and the third condition, and the personalized data satisfies the second condition, determining, based on the first scanning data, the correction profile relating to the imaging device.

13. A method implemented on a computing device having at least one processor, at least one computer-readable storage medium, and a communication port connected to a medical device including a detector, the detector including detector blocks, the method comprising:
  obtaining data relating to the medical device;
  determining, based on the data relating to the medical device, that the medical device satisfies a first condition;
  obtaining, based on first scanning data relating to a first subject, a first correction profile, the first scanning data including personalized data relating to the first subject and raw data relating to radiation events occurred in a positron emission tomography (PET) scan of the first subject, the raw data satisfies a second condition and the personalized data satisfies a third condition;
  updating, in response to the determination that the medical device satisfies the first condition, a second correction profile based on the first correction profile; and
  wherein the second condition includes that a count of the radiation events equals or exceeds a first threshold.

14. The method of claim 13, wherein the method further comprising: determining whether the medical device performs an application relating to the second correction profile, the application including at least one of a clinical examination application or a service examination application, and in response to determining that the medical device performs the application, obtaining the data relating to the medical device.

15. The method of claim 13, further comprising:
  obtaining second scanning data relating to a second subject based on the first correction profile; and
  generating an image based on the second scanning data.

16. The method of claim 13, wherein the data relating to the medical device includes a response rate of each of the detector blocks, and the determining, based on the data relating to the imaging device, that the imaging device satisfies the first condition further includes:
  acquiring a first group of detector blocks, each detector block of the first group having a response rate lower than a second threshold or exceeding a third threshold;
  determining whether a detector block count of the detector blocks belonging to the first group exceeds a fourth threshold; and
  in response to determining that the detector block count of the detector blocks belonging to the first group exceeds the fourth threshold, determining, that the imaging device satisfies the first condition.

17. The method of claim 13, wherein the data relating to the imaging device includes second scanning data relating to a second subject detected by the imaging device, and the determining, based on the data relating to the imaging device, that the imaging device satisfies the first condition, comprises:
  extracting first feature data from the second scanning data relating to the second subject; and
  determining, based on the first feature data, whether the imaging device satisfies the first condition.

18. The method of claim 13, wherein the first condition relates to a parameter of the imaging device, the parameter including at least one of a sensitivity of the detector, a spatial resolution of the imaging device, an energy resolution of the imaging device, or a time resolution of the imaging device.

* * * * *